United States Patent [19]

Cashion et al.

[11] Patent Number: 5,017,478

[45] Date of Patent: May 21, 1991

[54] TRANSFECTED CELLS CONTAINING PLASMIDS HAVING GENES ORIENTED IN OPPOSING DIRECTIONS AND METHODS OF USING

[75] Inventors: Linda Cashion, San Carlos; Kathi Begley, San Francisco, both of Calif.; Wendy Colby, Sisters, Oreg.; Michael J. Morser, San Francisco, Calif.

[73] Assignee: Berlex Laboratories, Inc., Cedar Knolls, N.J.

[21] Appl. No.: 251,159

[22] Filed: Sep. 29, 1988

Related U.S. Application Data

[63] Continuation-in-part of Ser. No. 74,083, Jul. 16, 1987, abandoned.

[51] Int. Cl.$^5$ .................. C12N 15/00; C12N 15/63; C12N 15/79
[52] U.S. Cl. .................. 435/69.1; 435/320.1; 435/255; 435/240.2; 435/212; 435/172.3; 435/70.1; 536/27; 935/60; 935/65; 935/27; 935/33; 935/36; 935/69; 935/70
[58] Field of Search .................. 435/68, 70, 235, 91, 435/317.1, 172.3, 320, 240.2; 536/22; 935/32, 34, 57, 60, 68, 27, 33, 70, 71, 69.1, 255, 240.2, 212, 70.1

[56] References Cited

U.S. PATENT DOCUMENTS

4,399,216  8/1983  Axel et al. .
4,634,665  1/1987  Axel et al. .

FOREIGN PATENT DOCUMENTS

0117059  8/1984  European Pat. Off. .
0117060  8/1984  European Pat. Off. .

OTHER PUBLICATIONS

Chakrabarty et al. (1985) Mol Cell Biol 5:3403–3409.
Pennica et al. (1983) Nature 301:214–221.
McLimans (1979) in Methods Enzymol. LVIII, pp. 194–211.
Haynes, J. et al., "Constitutive, Long-Term Production of Human Interferons by Hamster Cells Containing Multiple Copies of a Cloned Interferon Gene," *Nuc. Acids Res.*, vol. 11, No. 3, pp. 687–693 (1983).
Arathoon, W. R. et al., "Large-Scale Cell Culture in Biotechnology," *Science*, 232:1390–1395 (Jun. 13, 1986).
McDevitt, M. A. et al., "Sequences Capable of Restoring Poly(A) Site Function Define Two Distinct Downstream Elements," *The Embo Journal*, vol. 5, No. 11, pp. 2907–2913 (1986).
Wigler, M. et al., "Transfer of Purified Herpes Virus Thymidine Kinase Gene to Cultured Mouse Cells," *Cell*, 11:223–232 (1977).
Wigler, M. et al., "Transformation of Mammalian Cells with Genes from Procaryotes and Eucaryotes," *Cell*, 16:777–785 (1979).
Giri, I. et al., "Comparative Studies of the Expression of Linked Escherichia coli gpt Gene and BPV-1 DNAs in Transfected Cells," *Virology*, 127:385–396 (1983).
Southern, P. J. et al., "Transformation of Mammalian Cells to Antibiotic Resistance with a Bacterial Gene (List continued on next page.)

*Primary Examiner*—Richard A. Schwartz
*Assistant Examiner*—S. L. Nolan
*Attorney, Agent, or Firm*—Townsend and Townsend

[57] ABSTRACT

This invention relates generally to recombinant DNA techniques and to the expression of mammalian polypeptides in genetically engineered eukaryotic cells. Specifically, the invention relates to preferred plasmid constructs and methods that increase levels of expression of a cloned gene product. These preferred plasmids have selectable and nonselected gene cassettes adjacent to each other and oriented in the opposite direction for transcription. Such an orientation enhances overall levels of expression for the nonselected gene. Further, this invention relates to gene products expressed at these very high levels by the herein described method, and to the eukaryotic cells derived thereby.

21 Claims, 9 Drawing Sheets

OTHER PUBLICATIONS

Under Control of the SV40 Early Region Promoter," *J. Mol. Appl. Genet.*, 1:327–341 (1982).

Roginski et al., "Coordinate Modulation of Transfected HSV Thymidine Kinase and Human Globin Genes," *Cell*, 35:149–155 (1983).

Emerman, M. et al., "Genes with Promoters in Retrovirus Vectors Can be Independently Suppressed by an Epigenetic Mehcanism," *Cell*, 39:459–467 (1984).

Proudfoot, N. J., "Transcriptional Interference and Termination Between Duplicated α-Globin Gene Constructs Suggests a Novel Mechanism for Gene Regulation," *Nature*, 322:562–565 (1986).

Kaufman, et al., "Coamplification and Coexpression of Human Tissue-Type Plasminogen Activator and Murine Dihydrofolate Reductase Sequences in Chinese Hamster Ovary Cells," *Mol. Cell. Biol.*, 5:1750–1759 (1985).

Kaufman et al., "Amplification and Expression of Sequences Cotransfected with a Modular Dihydrofolate Reductase Complementary DNA Gene," *J. Mol. Biol.*, 159:601–621 (1982).

LEGEND

-  HARVEY SARCOMA VIRUS (HaSV) LONG TERMINAL REPEAT (LTR)
-  HaSV 3' UNTRANSLATED
-  HERPES SIMPLEX VIRUS THYMIDINE KINASE PROMOTER (tk)
-  tk POLY A ADDITION SITE (A+)
-  tk SEQUENCE 3' TO A+ SITE (HSV TERM)
-  SV40 EARLY PROMOTER
-  HARVEY'S 5' UNTRANSLATED
-  SV40 T INTRON
-  SV40 POLY A ADDITION SITE (A+): Bcl-Bam (EARLY)
-  SV40 POLY A ADDITION SITE (A+): Bam-Bcl (LATE)
-  t-PA GENOMIC
-  t-PA cDNA
-  HYGROMYCIN (hmb)
-  NEOMYCIN (neo)
-  neo 3' UNTRANSLATED
-  PI PROMOTER
-  dhfr
-  FRAGMENT OF TETRACYCLINE RESISTANCE GENE
-  FRAGMENT OF CHLORAMPHENICOL RESISTANCE GENE

FIG._1.

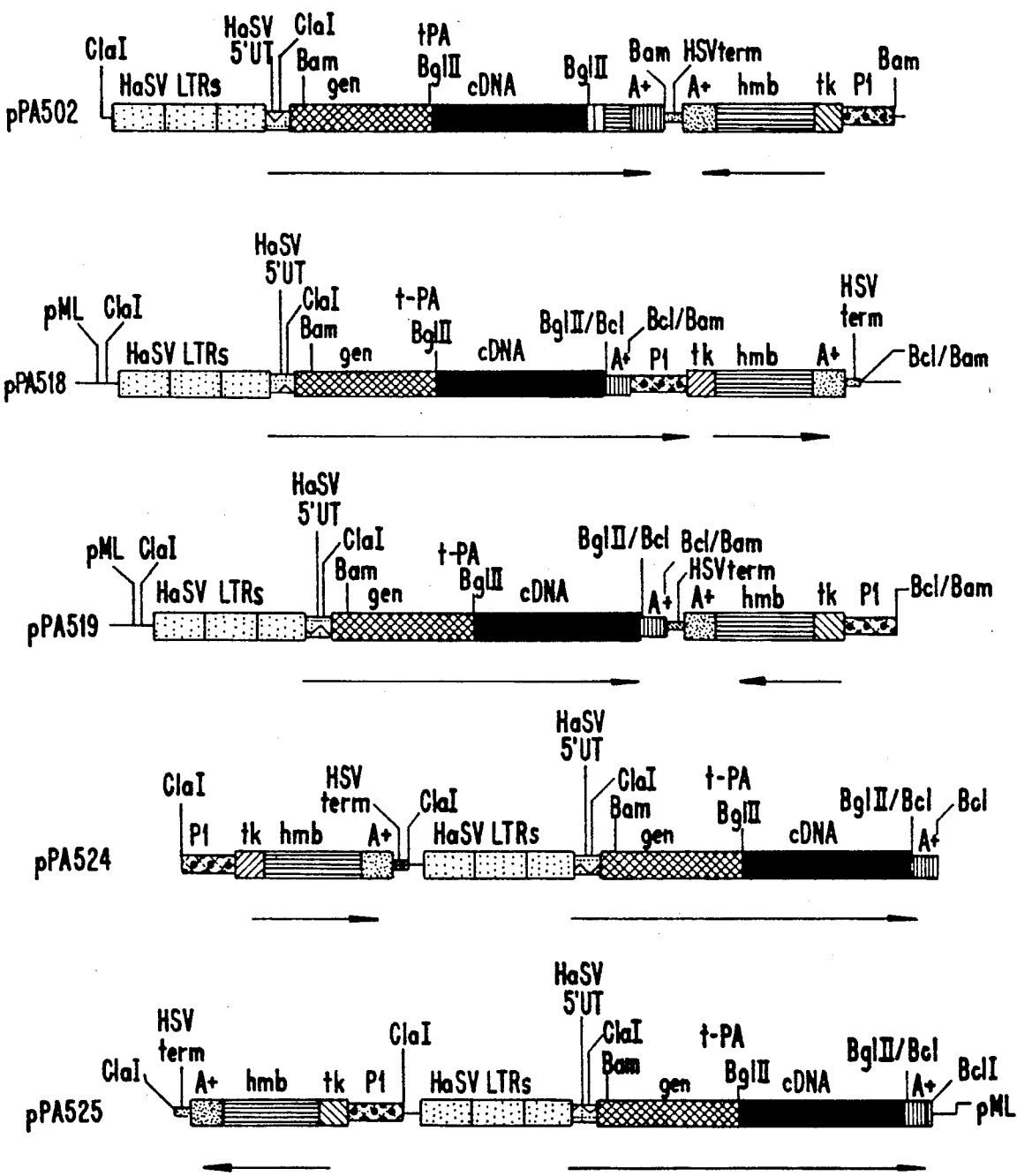
FIG._1A.

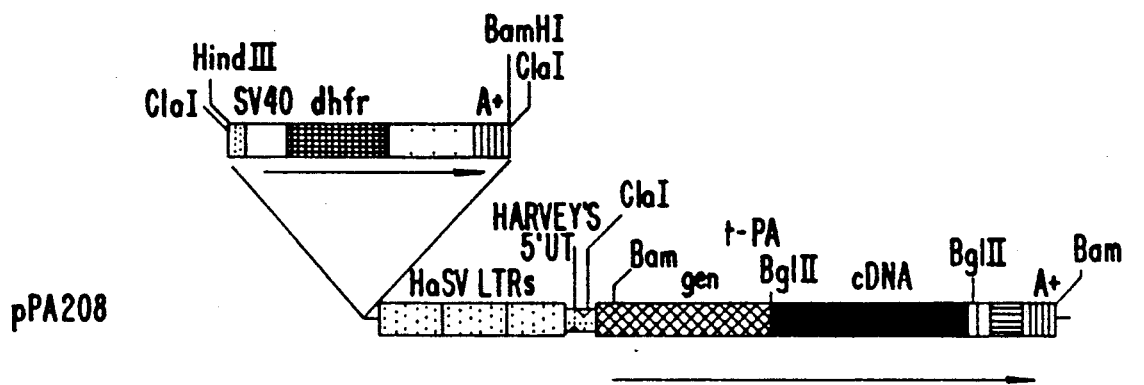
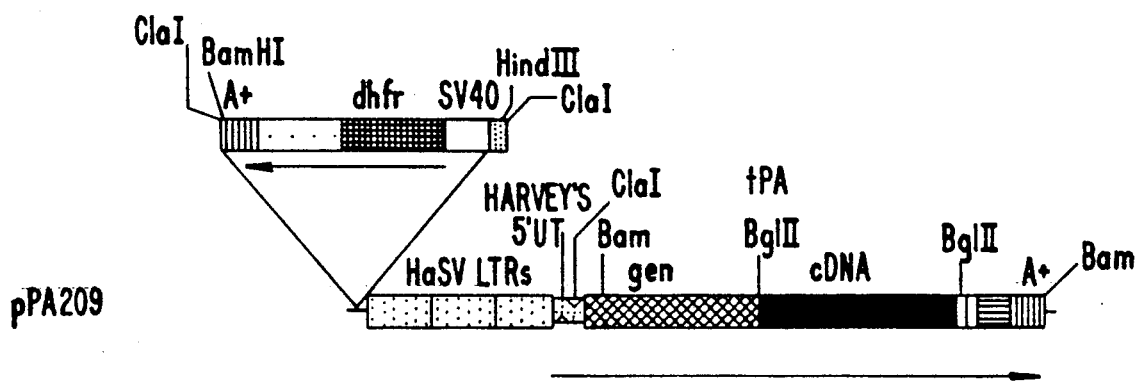
FIG._1B.

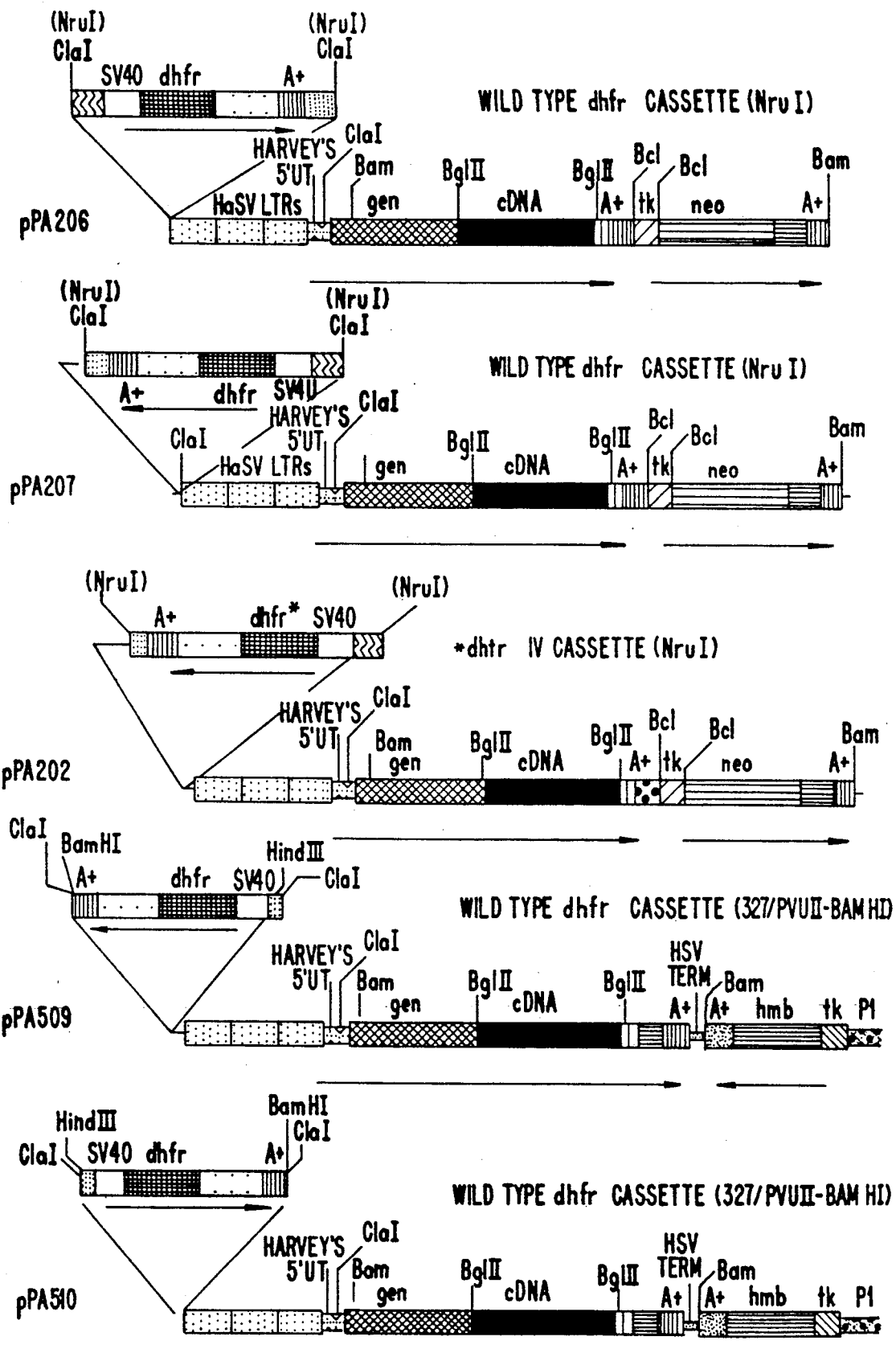
FIG._1C.

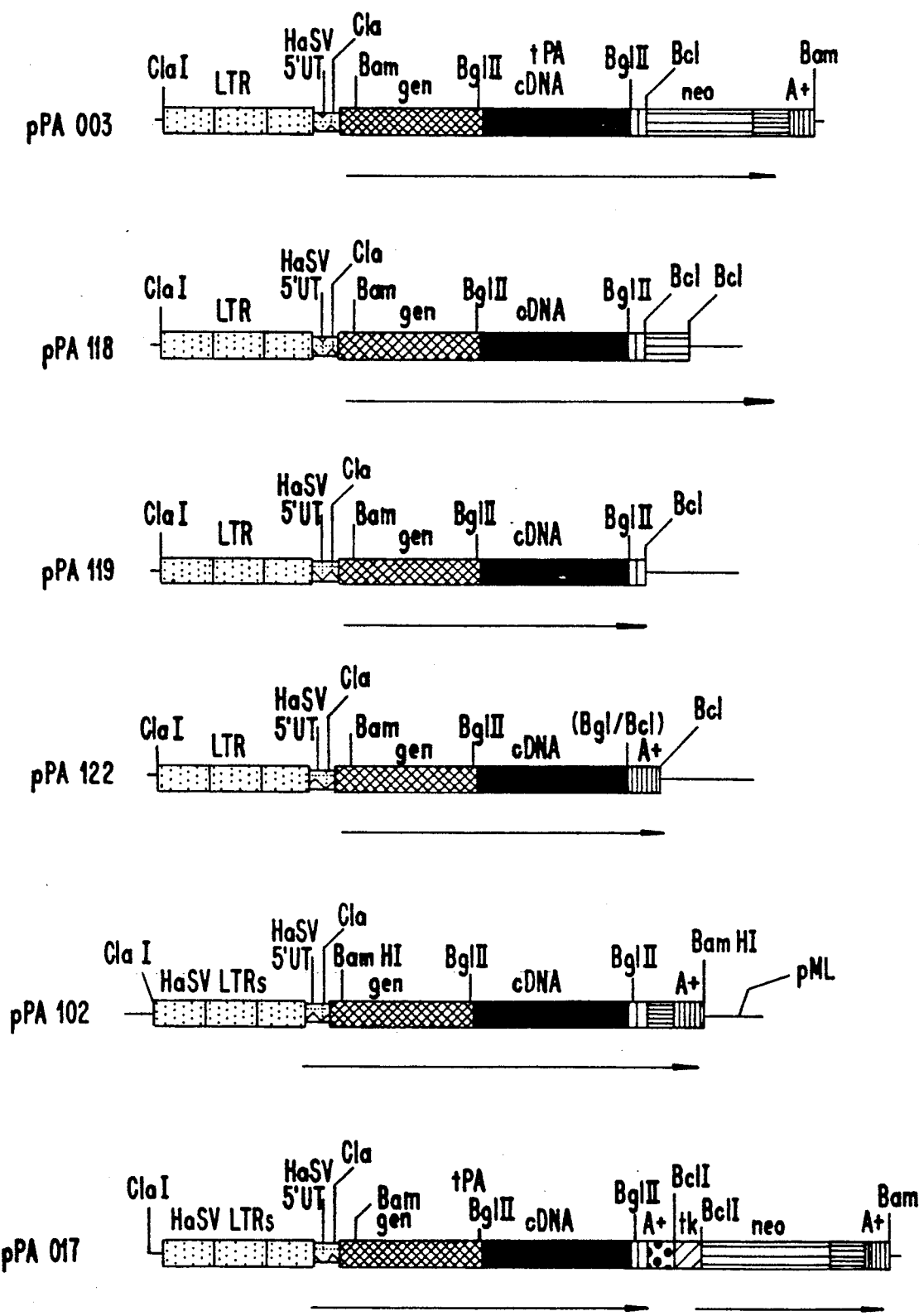
FIG._1D.

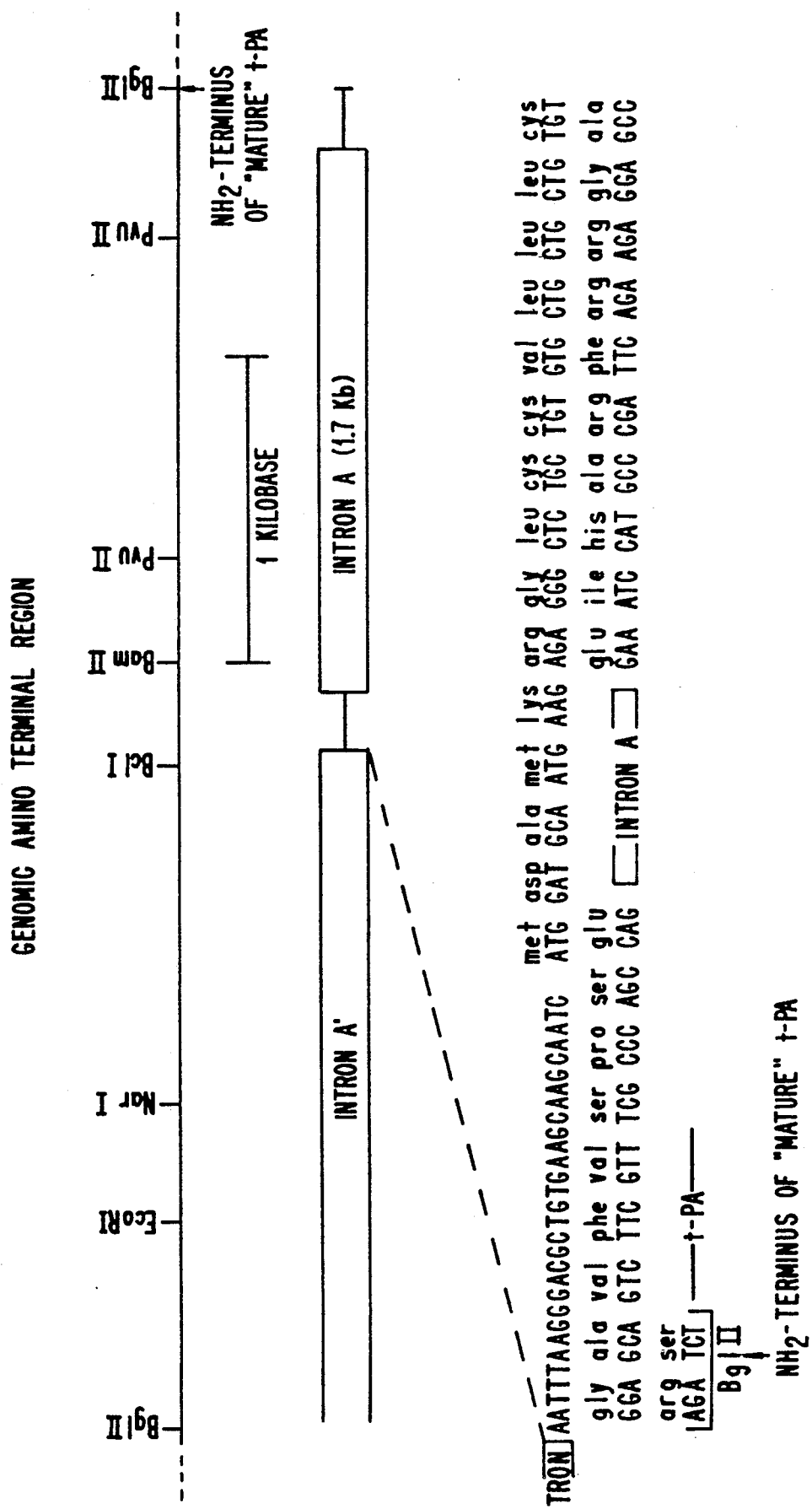
FIG_2A.

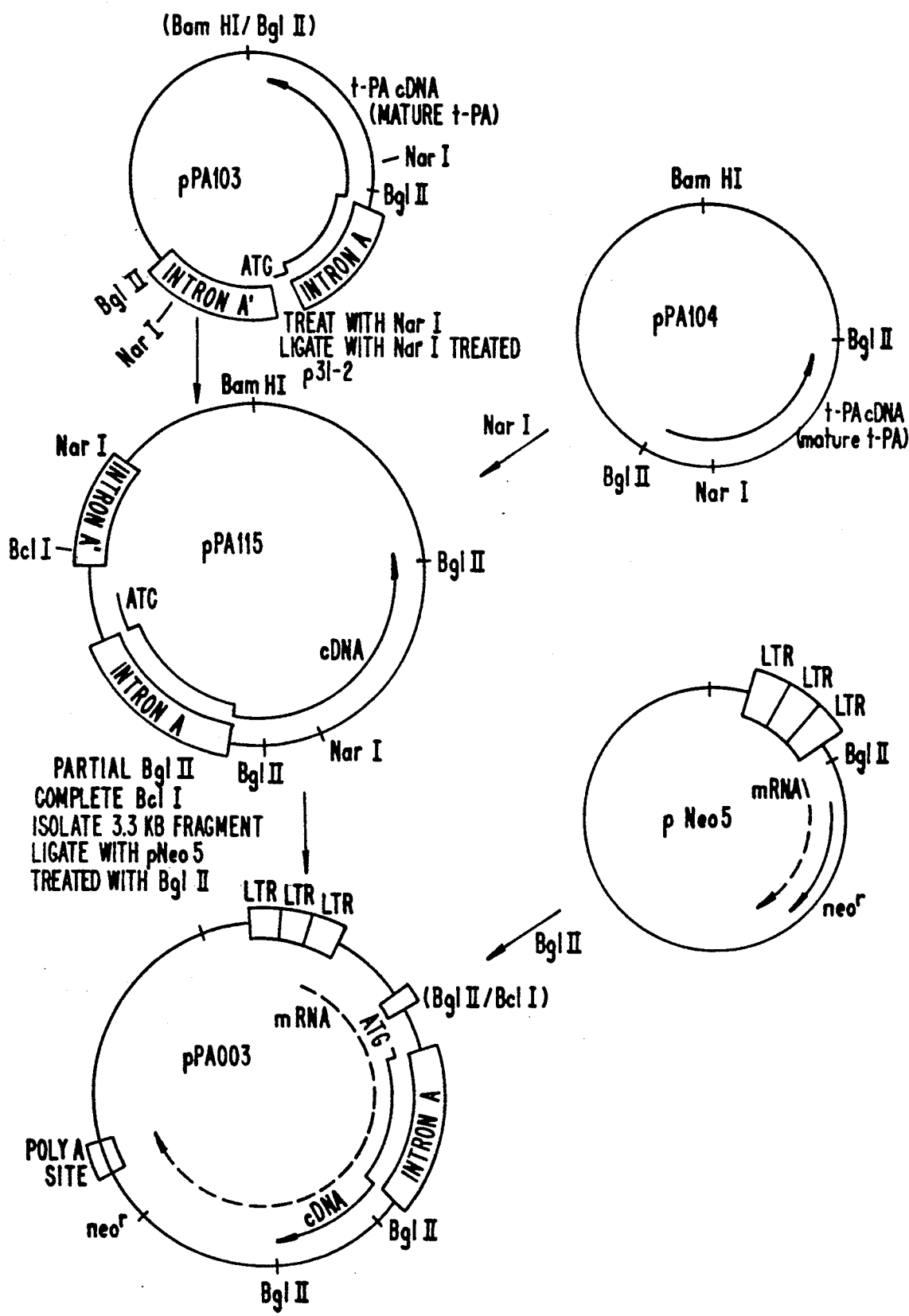
FIG._2B.

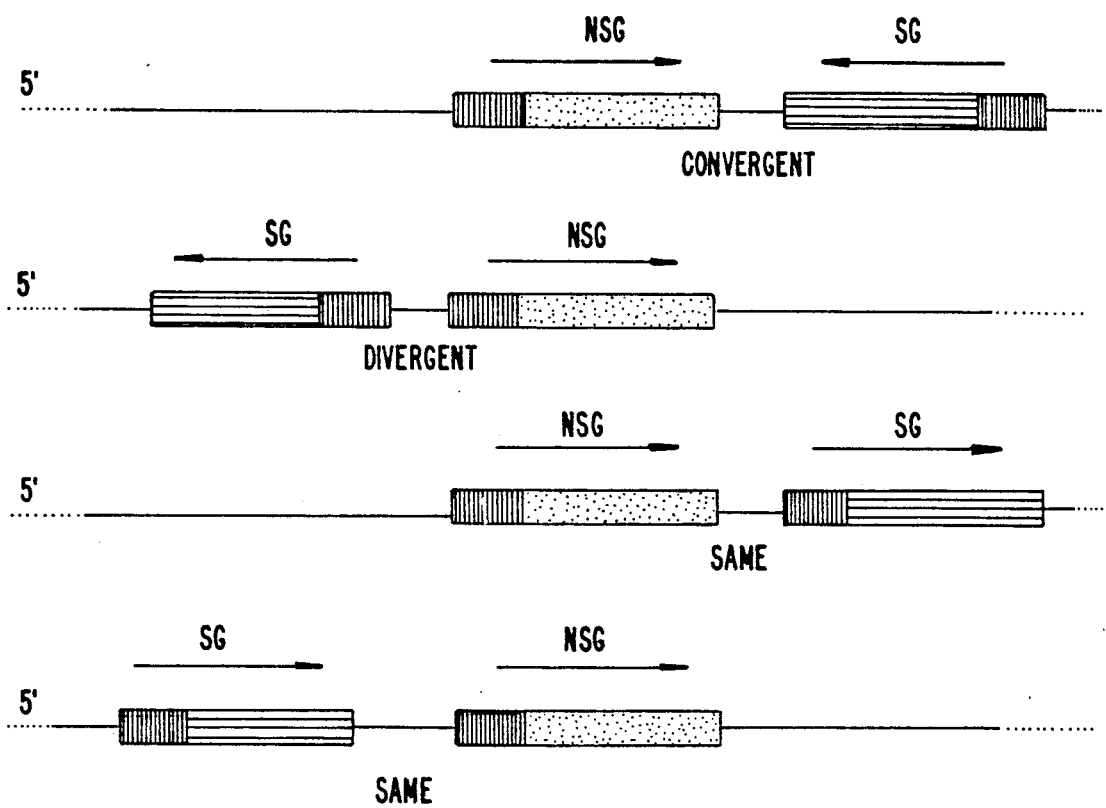
FIG._3.

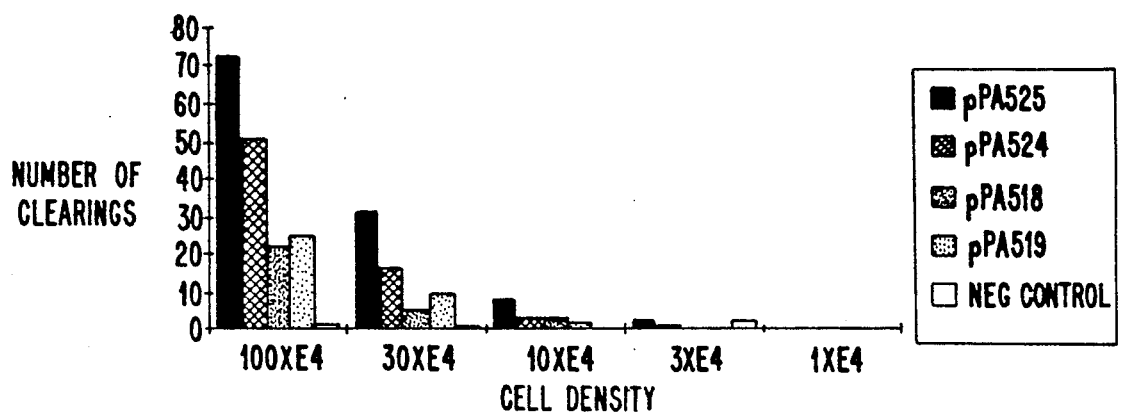
FIG._4.
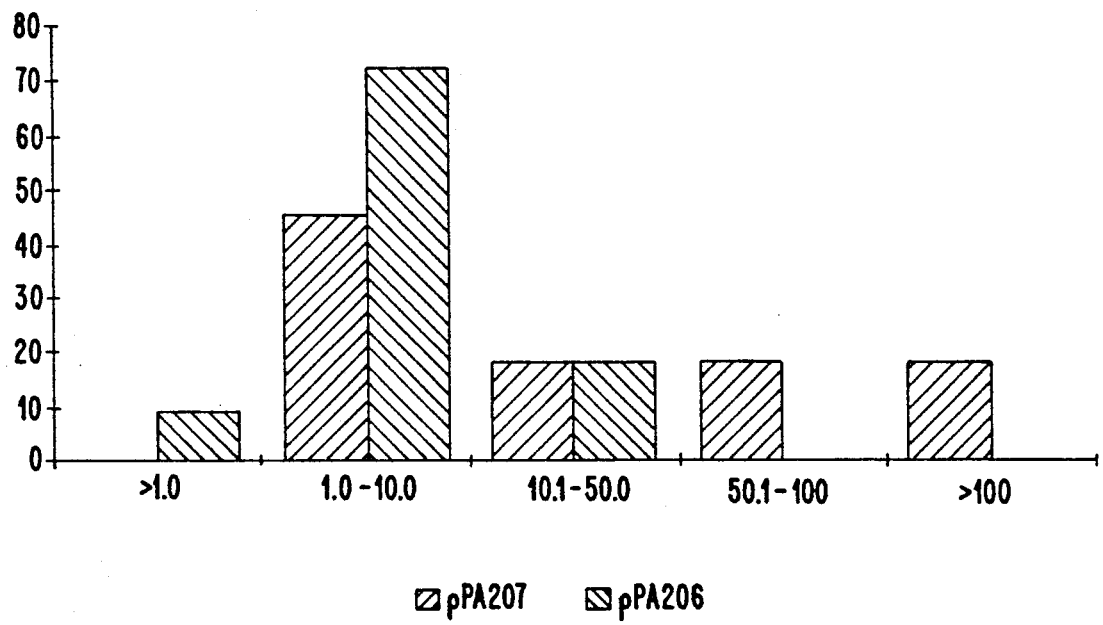
FIG._5.

TRANSFECTED CELLS CONTAINING PLASMIDS HAVING GENES ORIENTED IN OPPOSING DIRECTIONS AND METHODS OF USING

RELATED APPLICATIONS

This application is a continuation-in-part of U.S. Pat. application Ser. No. 074/083, filed July 16, 1987, now abandoned.

BACKGROUND OF THE INVENTION

1. Field of the Invention

This invention relates generally to recombinant DNA techniques and to the expression of mammalian polypeptides in genetically engineered eukaryotic cells. Specifically, the invention relates to preferred plasmid constructs and methods that increase levels of expression of a cloned gene product. These preferred plasmids have selectable and nonselected gene cassettes adjacent to each other and oriented in the opposite direction for transcription. Such an orientation enhances overall levels of expression for the nonselected gene. Further, this invention relates to gene products expressed at these very high levels by the herein described method, and to the eukaryotic cells derived thereby. 2. Background and Prior Art The ability to produce cloned gene products in eukaxyotic cell culture is often desirable, particularly when the cloned gene encodes a eukaryotic polypeptide, since prokaryotes lack a number of elements contained in eukaryotic cells. Such elements include the eukaryotic signals for transport, modification and glycosylation. Proper eukaryotic post-translational modification is often necessary for normal function of the final recovered protein. The eukaryotic gene product is most similar to or the same as the natural gene product when the cloned gene is expressed in a eukaryotic cell.

Early transfection experiments of Wigler, M. et al (Cell 11: 223-232 1977) were effective but inefficient. Since Axel first described cotransformation to increase the efficiency of transfecting foreign DNA into host cells (U.S. Pat. No. 4,399,216 and Wigler et al. Cell 16: 777-788, 1979), it has become common to have a drug resistance selection marker and a non-selectable gene of interest on the same plasmid as separate transcription units, each with their own promoter (Girli, I., Jouanneau, J. and Yabiv, M., 1983, Virology 127: 385-396 and Southern, P. J., Berg, P., 1982, J. Mol. Appl. Genet. 1:327-341). Expression levels of the non-selectable gene vary greatly in the individual transfected clones arising from experiment to experiment.

The current methodology usually includes first selecting a population of cells containing the transfected plasmid on the basis of drug resistance. This population is then screened for the introduction of a non-selectable gene, either by assaying for the non-selectable gene product, or for the presence of the genetic material comprising the coding sequence of the non-selectable gene. This method allows for the stable introduction into cultured mammalian cells of any cloned gene, and the systematic isolation of such cells.

A major issue in this area of research is the need to develop systems which can provide high levels of expression of the gene of interest in a reliable and reproducible way. Several methods to improve gene expression have been used successfully.

Expression of one gene in a multi-gene plasmid may be affected by other gene in the plasmid. Roginski et al. (Cell 35: 149-155, 1983) constructed a plasmid containing three transcription units. Clones were selected using the TK selection system and the expression of the non-selectable globin gene was analyzed. This group found coordinate expression of all three genes in 8 of the 10 clones examined. However, two other groups (Emiman, M. and Temin, H. M., Cell 39, 459-467, 1984 and; Proudfoot, N. J., Nature 322:562-565, 1986) have described the effect of transcriptional interference on adjacent cistrons. In these tWo examples, the expression of one gene had a negative effect on the expression of the adjacent gene.

Gene amplification is proven to be a method frequently used to increase expression levels. Gene amplification is often induced by exposure of sensitive cells to stepwise increases in antifolates, such as methotrexate (MTX), in the growth medium. This amplification can yield cells which are resistant to high levels of MTX and have increased levels of production of other associated genes as well (European Patent Application Nos. 0117059, 00117060 and Kaufman et al. (1985) Mol. Cell. Biol. 5:1750-1759, 1985).

However, gene amplification has several drawbacks including the instability of resultant clones, and the need to grow cultures in presence of high level of carcinogens (Kaufman and Sharp, J. Mol. Biol., 159:601-621, 1982).

In general, increased production of foreign proteins in a host through gene amplification techniques has been primarily limited to the use of mutant hosts. This is often undesirable for a number of reasons, most notably, that the mutant cell host most suitable for production of the foreign protein is unavailable. The expression of genes into fully active proteins commonly requires a specific cell type, which may not be available with the necessary mutation.

SUMMARY OF THE INVENTION

This invention provides for eukaryotic cell lines which express a desired gene product, comprising host cells transfected with at least one recombinant expression plasmid wherein the expression plasmid comprises a selectable gene cassette and a second gene cassette encoding the desired gene product with the priviso that the selectable gene cassette and the second gene cassette are disposed adjacent to each other in opposite and divergent transcriptional orientation. According to the present invention the desired gene product of the cell lines described is expressed at higher levels relative to host cells transfected with identically situated plasmids having either the second gene alone or the selectable gene cassette and the second gene cassette oriented in the same direction.

Preferred selectable gene cassettes are those that contain sequences that encode a protein selected from the group consisting of dihydrofolate reductase, neomycin phosphotransferase, and hygromycin phosphotransferase. The eukaryotic cell line may express desired gene products that are either selectable or non-selectable, and the desired gene products can either be heterologous or endogenous to the host cell.

Preferred desired genes encode a human pharmaceutical selected from the group consisting of hormones, immunogens, anti-cancer agents, antibiotics, immunoglobins, anti-allergy agents, or thrombolytic preparations. The preferred non-selectable gene encodes tissue plasminogen activator of the human variety. The desired genes encoding t-PA can optionally, but preferrably, contain introns such as a cDNA/genomic hybrid gene. Preferred t-PA expression vectors are pPA003, pPA509, and pPA202.

The eukaryotic cell lines are preferably selected from the group consisting of mammalian cells, insect cells, or yeast cells. For production of t-PA it is preferred that the cell line contain an endogenous t-PA gene and most preferred as host cells are human melanoma cells. Most particularly preferred are the cells designated CHL-1 (CRL 9446) and CHL-2 (CRL 9451). Even more preferred are those cells producing t-PA at a rate of at least about 4 milliunits per cell per day of t-PA.

BRIEF DESCRIPTION OF THE DRAWINGS

FIGS. 1a–d are diagramat gene maps of plasmids pPA502, pPA518, pPA519, pPA524, pPA525, pPA208, pPa209, pPA206, pPA207, pPa202, pPA509, pPA510, pPA003, ppA118, ppA119, pPA122, pPA102, pPA017.

FIG. 2 illustrates the steps leading to the construction of transfection plasmid pPA003.

a. The DNA sequence of the amino terminal region of the t-PA gene extending from intron A through the coding region and 5'—untranslated region to intron A'. The dashed line shows the structure and sequence of the amino terminal region of the t-PA chromosomal gene as it is fused to t-PA cDNA to generate a hybrid genomic DNA-cDNA gene.

b. The Nar I fragment of pPA103 extending from intron A to a Nar I site in t-PA cDNA was inserted into pPA104. This allowed removal of a 3.3 Kb BclI-Bgl II fragment containing the Bgl II site. This fragment was ligated into pneo5 resulting in pPA003, the genomic hybrid t-PA expression plasmid.

FIG. 3. Graphic description of gene orientation on a plasmid. Structural gene cassettes—both selectable and non-selectable genes are indicated by bars. Promoters are indicated and arrows are drawn to illustrate the direction of transcription of the genes relative to one another.

FIG. 4. An analysis of the expression of t-PA plasmids in C127 cells. C127 cells were transfected with plasmids pPA518, pPA519, pPA524, and pPA525 as well as a control plasmid lacking the LTR promoters and then plated into 100 mm perti dishes at different densities. The plates were overlaid with agarose containing fibrin and plasminogen as described in the text. One week later the number of clearings was counted. The graph is a plot of the number of clearings verus the cell density.

FIG. 5. Shows the production of t-PA by CHO cells transfected with pPA206 and pPA207. The medium from 11 clones was assayed for production.

DETAILED DESCRIPTION OF THE PREFERRED EMBODIMENT

Novel methods using recombinant expression vectors are provided for increasing the expression levels of a desired protein in a eukaryotic cell. In accordance with the present invention, eukaryotic cells capable of such are obtained by transformation with vectors containing at least one selectable gene cassette in addition to a structural gene cassette encoding the desired polypeptide. The invention relates to the orientation of gene cassettes within an expression vector. The vectors described herein contain the selectable gene cassette and the desired gene cassette adjacent to one another so that the genes are transcribed into mRNA in opposing directions with respect to one another. It is an aspect of the invention that the orientation of the gene cassettes not only be opposing, but divergent as well. The diagram of FIG. 3 graphically illustrates the terminology. Such vectors will also include appropriate regulatory sequences for self-replication, and selection in the appropriate host systems.

The use of these vectors and cell lines transfected with these vectors represents a significant improvement over prior expression systems. By the use of the plasmid design described herein and transfection of eukaryotic cells with such, one can achieve levels of expression that exceed levels reached when the selectable gene cassette and the gene cassette encoding the desired gene are adjacent but oriented in either the same direction of transcription or in a convergent direction of transcription with respect to one another.

The described method is operable and useful in a number of host cells which are adapted to tissue culture. Typically, the cells are eukaryotic, preferably human cells, that can grow rapidly in standard media preparations. Substantially any non-microbial cell, whether or not transformed, and which is prevented from growth by a selective agent will find use in the present invention.

This invention involves a series of molecular genetic manipulations that can be achieved in a variety of known ways. Prototype vectors and cell lines have been deposited in accordance with the Budapest Treaty. Plasmids pPA003, pPA202, and pPA509 are maintained in and E. coli host and are illustrated in FIG. 1. Plasmid ppA003 was transfected into the cell line CHL-1 and a stable transfectant, CHL-2 was isolated. These plasmids and cell lines were deposited pursuant to the Budapest Treaty with the American Type Culture Collection, 12301 Parklawn Drive, Rockville, Md. 20852 (USA), and given the accession numbers: pPA003 deposited on Jan. 13, 1987 and assigned ATCC 67293; pPA202 deposited on June 18, 1987 and assigned ATCC 67446, pPA509 deposited on June 18, 1987 and assigned ATCC 67443, CHL-1 deposited on June 18, 1987 and assigned CRL 9446 and CHL-2 deposited on June 19, 1987 and assigned CRL 9451. The deposited plasmids and cell lines should not be construed as a limitation of this invention in any manner. Although a convenient starting material, the following will detail various methods available to create equally suitable expression cassettes from alternative starting materials.

GENERAL METHODS

Generally, the definitions of nomenclature and descriptions of general laboratory procedures used in this application can be found in Maniatis, T. et al., Molecular Cloning, A Laboratory Manual, Cold Spring Harbor Laboratory, Cold Spring Harbor, N.Y., 1982. The manual is hereinafter referred to as Maniatis.

All enzymes were used according to the manufacturer's instructions.

Nucleotide sizes are given in either kilobases (kb) or basepairs (bp). These are estimates derived from agarose or acrylamide gel electrophoresis or from published DNA sequences.

Oligonucleotides that are not commercially available can be chemically synthesized according to the solid phase phosphoramidite triester method first described by Beaucage S. L. and Caruthers, M. H. Tetrahedron Letts. 22(20):1859–1862 (1981) using an automated synthesizer, as described in Needham-VanDevanter, D. R., et al., Nucleic Acids Res., 12:6159–6168 (1984). Purification of oligonucleotides was by either native acrylamide gel electrophoresis or by anion-exchange HPLC as described in Pearson, J. D. and Regnier, F. E., J. Chrom., 255:137–149 (1983).

The sequence of the synthetic oligonucleotides can be verified using the chemical degradation method of Maxam, A. M. and Gilbert, W., Grossman, L. and Moldave, D., eds., Academic Press, New York, Methods in Enzymology, 65:499–560 (1980). Alternatively, the sequence can be confirmed after the assembly of the oligonucleotide fragments into the double-stranded DNA sequence using the method of Maxam and Gilbert, supra, or the chain termination method for sequencing doublestranded templates of Wallace, R. B., et al., Gene, 16:21–26 (1981).

This invention relates to cloning and use of expression vectors in eukaryotic cells. Intermediate vectors are cloned for amplification in prokaryotes such as Escherchia, Bacillus and Streptomyces. Most preferred is E. coli because that organism is easy to culture and more fully understood than other species of prokaryotes. The Maniatis manual contains methodology sufficient to conduct all subsequently described clonings in E. coli. Strain MH-1 is preferred unless otherwise stated. All E. coli strains are grown on Luria broth (LB) with glucose, or M9 medium supplemented with glucose and acid-hydrolyzed casein amino acids. Strains with resistance to antibiotics were maintained at the drug concentrations described in Maniatis. Transformations were performed according to the method described by Morrison, D. A. (1977), J. of Bact., 132:349–351 or by Clark-Curtiss, J. E. and Curtiss, R., 1983, in Methods in Enzymology, 101:347–362, Wu, R., Grossman, L. and Moldave, K., eds., Academic Press, New York. Representative vectors include pBR322 and the pUC series which are available from commercial sources.

The host cells are competent or rendered competent for transfection by various means. There are several well-known methods of introducing DNA into aminal cells. These include: calcium phosphate precipitation, fusion of the recipient cells with bacterial protoplasts containing the DNA, treatment of the recipient cells with liposomes containing the DNA, electroporation and micro-injection of the DNA directly into the cells.

B. CLONING VECTORS

Cloning vectors suitable for replication in prokaryotes or eukaryotes and containing transcription terminators useful for regulation of the expression of downstream structural proteins are described herein. The disclosed vectors are comprised of expression cassettes containing at least one independent terminator sequence; sequences permitting replication of the plasmid in both eukaryotes and prokaryotes, i.e., shuttle vectors; and selection markers for both the prokaryote and eukaryote systems.

In order to select the transformed bacteria, selectable markers must be incorporated into the cloning vectors. These markers permit the selection of bacterial colonies containing the vectors which one desires to replicate. Examples of selectable markers include for E. coli: genes specifying resistance to antibiotics, i.e., ampicillin, tetracycline, chloramphenicol, kanamycin, erythromycin, or genes conferring other types of selectable enzymatic activities such as b-galactosidase. There are numerous other markers both known and unknown which embody the above scientific principles, all of which would be useful as markers to detect those bacteria transformed with the vectors embraced by this invention.

C. SELECTABLE MARKERS FOR EUKARYOTIC CELLS

In order to select the transfected eukaryotic cells, suitable eukaryote markers must be incorporated into the cloning vectors. These markers may permit selection of transfected cells by virtue of survival in an otherwise lethal environment utilizing the same principles described for the prokaryote markers or the selectable markers may visibly alter the host cells allowing for easy detection. A general overview of this art is found in P. J. Southern and Berg, P. J. Mol. App. Gen. 1: 327–41 (1982).

Examples of selectable markers include the dihydrofolate reductase gene (dhfr), an altered dhfr gene (dhfr-IV), the hygromycin B resistance gene (hmb), the neomycin phosphotransferase II gene (neo) and the adenosine deaminase gene for the human melanoma cell line RPMI 7932 (Bowes) cells, Chinese hamster cells, C127 murine cells and other higher eukaryotic cells; and the enzyme, b-galactosidase and the nuclear polyhedral virus from Autographa californica for insect cell lines from Spodoptera frugiperda and Bombyx mori; and for yeast, Lue-2, URA-3, Trp-1, and His-3 are known selectable markers (Gene 8:17–24, 1979). There are numerous other markers both known and unknown which embody the above scientific principles, all of which would be useful as markers to detect those eukaryotic cells transfected with the vectors embraced by this invention.

It is also conceivable that the desired structural gene might also operate as a selectable marker and eliminate the need for a separate selectable marker in eukaryotic cell hosts.

For the preferred cell hosts RPMI 7932 cells expressing tissue plasminogen, the preferred selectable markers are neomycin phosphotransferase (neo), dihyrofolate reductase (dhfr), an altered dihydrofolate reductase (dhfr-IV), and phosphotransferase(hmb). The neo gene confers resistance to kanomycin in bacteria and to the aminoglycoside antibiotic G418 in eukaryotes (Southern, P. J., Berg, P., 1982, J. Mol. Appl. Genet. 1:327–341, Colbene-Garapin et al., J. Mol. Biol. 150:1–14, 1981). The dhfr gene confers on the cell resistance to methotrexate (MTX) (Subramani et al., Mol. Cell. Biol. 1:854–864, 1981). The dhfr-IV gene Was derived from the wild type mouse dhfr gene. By in vitro mutagenesis of the gene sequence, an enzyme with altered characteristics was isolated. This mutant has a dereased affinity for MTX. Thus, cells transformed with this gene are resistant to higher levels of MTX than those carrying the wild type gene. (Simonson, C., and Levinson, A., PNAS USA, 80:2495–2499, 1983). The hmb gene confers resistance to hygromycin B (Blochlinger, K., and Digglemann, H., Mol. Cell. Biol 4:2929–2931, 1984).

In another aspect, the selectable genes may be heterologous or endogenous to the host cell. Examples of heterologous selectable genes would be neo in RPMI 7932 cells, CHO cells, or Vero cells, or hmb in RPMI 7932, CHO, or Vero cells. The selectable gene may also be a gene that can be amplified. DHFR is an example of such a selectable/amplifiable gene.

In other instances, the expression vectors may comprises two or more selectable genes. This allows selection of transfectants using first one selection medium, and then a second selection medium. The level of expression of the desired gene product increases with each selection procedure.

Whatever selectable gene is chosen, it will be operably linked to one or more regulatory sequences, e.g., the gene will be placed in the expression vector adjacent to a promoter so that expression can occur. Typically, the structural gene will have its own host cell compatable promoter.

The eukaryotic cell lines useful in the practice of the present invention are wild-type or auxotrophic, such choice is governed by the particular selection marker used in the transfection plasmid. For example wild-type cells can be used with a dhfr selection marker although wild-type cells have an endogenous dhfr gene, but drug resistance selection markers require a host cell which is not resistant to that drug.

D. REPLICATION ORIGINS

The cloning vectors must contain an origin of replication suitable for directing replication in prokaryotes. For maintenance in eukaryotic hosts the vectors must either contain an origin of replication usually of viral origin or have the capacity to integrate into the host genome. There are numerous examples of origin of replications for prokaryotes. *E. coli* replicons, which are the most closely studied, have origins of replication which are temperature dependent, permit high copy replication or those which constitutively sustain plasmid copies at only lower moderate levels. Examples of *E. coli* origins of replication are ColE1 ori, R1 ori R, or pSC101 ori. After transfection into eukaryotic cells, the plasmids will either integrate into the host's genome or remain extrachromosomally replicating. In the embodiment exemplified, the plasmids described integrate into the host cell. Examples of non-integrating vectors include those derivatives from the Epstein Bar virus. Yates et al., Nature, 313: 812–814 (1985). There are numerous origins of replication both known and unknown which embody the above scientific principles, all of which would be useful to maintain the plasmids within the prokaryotic and eukaryotic hosts transformed, transfected or infected with the vectors embraced by this invention.

E. EUKARYOTIC HOST CELLS

Of the higher eukaryotic cell systems useful for the expression of desired proteins, there are numerous cell systems to select from. Illustrative examples of mammalian cell lines include RPMI 7932, VERO and HeLa cells, Chinese hamster ovary (CHO) cell lines, WI38, BHK, COS-7, C127 or MDCK cell lines. Cells suitable for use in this invention are commercially available from the American Type Culture Collection. Illustrative insect cell lines include Spodoptera frugiperda (fall Armyworm) and Bombyx mori (silkworm).

The disclosed embodiment makes use of CHL-1 cells. These are derived from RPMI 7932 cells, a readily available human cell line. The CHL-1 line is improved over the parental RPMI 7932 cell line. The CHL-1 cells, unlike the parental cells, have been cured of mycoplasma contamination, which is an opportunistic organism that frequently contaminates cells in long term culture and interferes with large scale, i.e. commercial, use in a production scheme. Further, the CHL-1 RPMI 7932 cell derivative can grow at high cell density than the parental cell line. CHL-1 cells are capable of growth to a density of $5 \times 10^7$ cells/ml; whereas the parental RPMI 7932 cells will grow to only $5 \times 10^6$ cells/ml under the same conditions.

F. EUKARYOTIC EXPRESSION CASSETTES

The eukaryotic expression cassettes are sequences of DNA which are functionally capable of directing the expression of proteins in a eukaryotic host. The cassettes are generically comprised of a functional promoter that permits the initiation of transcription, at least one structural gene and an appropriate 3' portion encoding the polyadenylation signal sequences necessary to terminate the transcription process. An example of a terminator sequence is the polyadenylation sequence from SV40. The cassettes may optionally contain a signal sequence in the 5' region of the structural gene that will direct post-translational processing of the structural gene.

i. Structural Genes

The structural gene may be essentially any DNA sequence (e.g., cDNA or genomic clone with introns) that upon expression codes for a desired polypeptide, including heterologous proteins or endogenous proteins or proteins naturally produced by the host cell. It may be prokaryotic or viral in origin; such as genes encoding antigens useful as vaccines or diagnostic tools. For example, it could be the feline leukemia viral coat protein, or a surface antigen or enzyme from a protozoan parasite such as *Ti Trypanisoma cruzi, Hypodermin lineatum, Mycoplasma hyopneumoniae,* or *Treponema hyodysenteriae.*

Typically, it will be a eukaryotic structural gene, the protein product of which has a commercial utility, particularly in medical applications. Thus, the polypeptides (typically from about 5,000 to 300,000 MW) can be any variety of proteins, such as enzymes, immunoglobulins, hormones, vaccines, receptors and the like. Examples of proteins falling within the above categories include tissue plasminogen activator, Factor VIII:C, interferons, insulin, growth hormone, growth factors, erythropietin, interleukins 1, 2, and 3, and others, as new genes are cloned and expressed. Importantly, the entire structural gene for the naturally occurring protein need not be expressed, as fragments or subunits may be produced as desired. If necessary, the proteins will contain leader sequences, transmembrance sequences or the like, depending upon the particular ultimate utility.

The precise structural gene incorporated into the expression vector is not critical to the practice of the present invention. In the preferred embodiment the gene for tissue plasminogen activator (t-PA) has been used to describe the current invention. The structural gene encode tissue plasminogen activator is not selectable by growth in any defined medium. T-PA production must be determined by assay of surviving transfectants. Other suitable non-selectable genes include by are not limited to human growth hormone, bovine growth hormone, erythropoetin, IgE, calf chymosin, glycosylation inhibiting factor (GIF), and urokinase.

ii. Promoters

There are an unlimited number of promoters available for expression in eukaryotes and the following is not meant to be a limitation of this invention nor a list of preferred promoters. The following promoters are simply some of the more well studied promoters available for expression in various hosts and alternative promoters would work equally well in this invention. Promoters useful for regulating the expression of heterologous proteins in mammalian or insect systems include but are not limited to the following: the retroviral long terminal repeat promoters (Nature, 297:479–483, 1982), SV-40 promoter (Science, 222:524–527, 1983), thymidine kinase promoter (Banerji, J., et al., Cell 27:299–308, 1982), or the beta-globin promoter (Luciw, P.A., et al., Cell 33:705–716, 1983). For yeast promoters, the following are useful for expression: GAL1,10 (Mol. and Cell. Biol., 4:1440-48, 1984); ADH2 (J. Biol. Chem. 258:2674–2682, 1983); PH05 (EMBO J. 6:675–680, 1982); and MFa1 (Herskowitz, I. & Oshima, Y. (1982) in The Molecular Biology of the Yeast Saccharomyces, (eds. Strathern, J. N., Jones, E. W., & Broach, J. R., Cold Spring Harbor Labs., Cold Spring Harbor, N.Y. pp. 181–209).

The promoters preferred for RPMI 7932 cells which are the preferred cells type for expressing tissue plasminogen activator will typically be any of the well known viral promoters derived from retroviruses, adenovirus, or simian virus 40 (SV40). (See, generally, Winnaker, E. L., Introduction to Gene Technology, VCH Pubklishers, N.Y. (1987), which is incorporated wherein by reference).

G. REGULATION OF EXPRESSION

This invention relates to the expression of desired proteins in eukaryotic host cells. It is expected that those of skill in the art are knowledgeable in the expression systems chosen for ultimate expression of any chosen protein and no attempt to describe in detail the various methods known for the expression of proteins in eukaryotes will be made. However, several general references are available which describe in detail the processes for expression of proteins in eukaryotic cell systems. These references cite two additional reference which give even greater detail. For example, the expression of proteins in yeast is generally described in Methods In Yeast Genetics, Sherman, F., et al., Cold Spring Harbor Laboratory (1982). Methodology for protein expression in higher eukaryotes is generally described in Eukaryotic Viral Vectors, Ed. Yakov Gluzman, Cold Spring Harbor Laboratory, 1982; and in B. Howard and M. McCormick, Vector mediated gene transfer (pp. 211–233); in I. Abraham, DNA mediated gene transfer (pp. 181–210) in Molecular Cell Genetics, Ed. Michael M. Gottesmann, John Wiley & Sons (1985); and in J. H. Miller and M. P. Calos, Gene Transfer Vectors for Mammalian Cells, Cold Spring Harbor Lab N.Y. (1987).

H. CULTURING CELLS

It is preferred that the host cell is capable of rapid growth in cell culture and able to glycosylate expressed gene products to ensure that the protein is produced in high quantity and resembles the naturally occurring material. Cells known to be suitable for dense growth in tissue culture are particularly desirable and in the art a variety of invertebrate or vertebrate cells have been employed whether normal or transformed.

The transfected cells are grown up by means well known in the art. For examples, see: Biochemical Methods in Cell Culture and Virology, Kuchler, R. J., Dowden, Hutchinson and Ross, Inc. (1977). The expression products are harvested from the cell medium in those systems where the protein is excreted from the host cell or from the cell suspension after disruption of the host cell system by, e.g., mechanical or enzymatic means, which are well known in the art.

I. TRANSCRIPTION ORIENTATION OF GENE CASSETTES

The disclosed methods provide enhanced production of a structural gene product in a eukaryotic host cell. According to the method, a eukaryotic host cell is transfected with at least one vector containing at least one selectable gene and a structural gene of interest. Each gene is operably linked to a promoter which allows that gene to be transcribed into mRNA. This promoter-gene cassette is transcribed unidirectionally; from the 5' portion of the gene, adjacent to the promoter, to the 3' portion of the gene adjacent to a terminator sequence. In the present invention plasmids are constructed wherein at least one selectable gene cassette is transcribed in the opposite and divergent direction as an adjacent structural gene of interest. In the divergent form the promoters of the selectable gene and the gene of interest are adjacent as diagrammed in FIG. 3.

Transfectants are selected by growth under suitable selective conditions according to the selectable gene present on the expression vector. A transfected cell may then be isolated and characterized.

The structural gene of interest and the selectable genes are operably linked to one or more regulatory DNA sequences. The resultant transfected cell line is then grown under appropriate conditions to allow for expression of the structural gene of interest, and followed by the subsequent purification and recovery of that structural gene product.

The disclosed methods provide plasmids wherein the adjacent promotors of the selectable gene cassette and the gene cassette encoding the desired protein are at most 2.0 kilobases apart. In the preferred embodiments the promoters of these adjacent gene cassettes are 100–1000 base pairs apart. Additionally, no other structural gene lies between the selectable gene and the gene of interest.

The plasmid encoded structural gene of the examples is endogenous to the host cell. It is also possible to practice the current invention to express proteins that are heterologous, that is, proteins whose DNA sequence is not normally present in the host cell.

According to the present invention, plasmids have been prepared which can be transfected into eukaryotic cells by virtue of a selectable gene. The selectable gene allows eukaryotic cells transfected with the plasmids of the present invention to be selectively grown in the presence of an agent.

The general method used to isolate clones has been to introduce purified plasmid DNA into cells that had been plated 24 hours previously by the calcium phosphate precipitation technique (Wigler PNAS 76: 1376–1376, 1979).

To compare the expression levels of transfectants generated with the plasmids, disclosed herein, a population of clones selected from a single transfection experiment was analyzed to determine t-PA expression as a mass culture value. Individual clones were then isolated from the population to determine the distribution of expression levels of clones within the population.

Numerous assays are available for determining the level of t-PA produced by cells in culture. These methods are described in detail in the following to references: Kruithof, et al., Thromb. Res., 28:251–260; Verheijen, J. H., et al., Thromb. Res., 39:281–288, 1985; Beebe, et al., Thromb. Res., 47:123–128, 1987; and Gaffney, P., et al., Thromb. and Haemos, 53:134–136, 1985.

All of the referenced cited above and below are considered to be available to those of skill in the art. They teach background art commonly used by those of skill. The salient sections of the references are hereby incorporated by reference.

Definitions

The term "adjacent" in the context of gene cassettes refers to cassettes disposed in a nonoverlapping manner no more than 2.0 kilobases apart, preferably between 100 and 1000 bases apart without a translatable region between the two cassettes.

The phrase "gene cassette" refers to to a complete unit of gene expression and regulation, including structural gene, regulating DNA sequences recognized by regulator gene products and a polyadenylation sequence to indicate the 3' end of a transcriptional unit.

The phrase "structural gene" refers to DNA sequences which code for any RNA or protein product other than a regulator protein.

The phrase "non-selectable gene" refers to a structural gene encoding a gene product for which no selective growth medium is known which would allow the experimenter to distinguish between clones which express the gene and clones which do not.

The phrase "operably linked" refers to sequences of DNA wherein one domain is capable of effecting, as a promoter, the transcription of a second domain which encodes a structural gene.

The phrase "expression vector" includes vectors which are capable of expressing DNA sequences contained therein, where such sequences are operably linked to other sequences capable of effecting their expression. In general, expression vectors of utility in recombinant DNA techniques are often in the form of "plasmids" which refer to circular double stranded DNA loops, which, in their vector form, are not bound to the chromosome. In the present specification, "plasmid" and "vector" are used interchangeably. However, the invention is intended to include such other forms of expression vectors which serve equivalent functions and which become known in the are subsequently hereto.

The term "host cells" refers to cells which can be grown in culture and are capable of being transformed or transfecting using plasmids and vectors as herein described.

The term "recombinant host cells" refers to cells which have been transformed with vectors constructed using recombinant DNA techniques.

"CHL-2" refers to a stable eukaryotic cell line derived from CHL-1 by transfection with a plasmid encoding t-PA, pPA003. This plasmid is described in the detailed description selection.

P__. This is a plasmid designation. "p" written before a set of letters and indicates that what is being referred to is a plasmid; e.g., pPA525.

t-PA (mu/c/d) Refers to a standardized amount of t-PA produced by a defined number of cells. The t-PA is measured by a fibrin plate assay. The assay is described in the detailed disclosure of this application. These units are defined as international units by comparison with the World Health Organization international standard.

The following examples are offered by way of illustration and not by way of limitation.

EXAMPLES

A primary object of the present invention is to provide conditions and plasmids that lead to high levels of production of a predetermined polypeptide. In the following examples, three parameters have been described: the selectable gene marker, the selection conditions, and host cells. The end result from the following experimental work is a production system that will economically produce the desired protein on a large scale. It will be readily apparent to those skilled in the art that a wide variety of genes of interest may be substituted in place of t-PA.

A. Design of the Expression Plasmids

The t-PA expression plasmids were constructed with dhfr, neo or hmb genes as selection markers. Promoters used on the described plasmids include LTR, SVe, and TK. These plasmids were used to determine if the level of t-PA expression could be increased by altering the position of the selection marker within the expression plasmid. Plasmids were constructed with the gene for the selectable marker either in front of (at the 5' end) or behind (at the 3' end) of the t-PA transcription unit. Moreover, within these two groups, pairs of plasmids were made such that the transcription of the selectable gene was in the same direction or the opposite direction as the t-PA gene (FIG. 3).

In this way, the transcription units can be oriented so that they are in the same direction or they can either converge or diverge. In the convergent form, the promoters for the two genes are separated, while in the divergent form they are adjacent. Additional plasmids were analyzed that contained two selectable markers at both the 5' and 3' positons of the t-PA gene.

B. Plasmid Construction i. pPA003

All base numbering for nucleotide positions of the t-PA encoding sequences correspond to the sequence numbering published by Pennica et al., "Cloning and Expression of Human Tissue-Type Plasminogen Activator cDNA in *E. coli*," Nature 301:214–221 (1983).

Plasmid PA003 (FIG. 1d) contains the t-PA gene and the neo gene both operably linked to the LTR promoter. This plasmid is constructed so that the LTR promoter controls the discistronic expression of t-PA. A description of the steps used to assemble this plasmid is described below and is depicted in FIG. 2A and B. Plasmid PA003 has been deposited with the ATCC and has accession number 67293.

PNeo-5 (Lusky, and Botchan, Cell 36:391–401, 1984) was used as the starting material for expression vector construction for t-PA. PNeo-5 contains the triple LTR promoter the neo gene and a polyadenylation sequence. The DNA sequences coding for t-PA were assembled from two sources: the 5'-end of the gene was from a human DNA gene library and the 3'-end was selected from a cDNA library made from CHL-1 mRNA. The isolation and assembly of the DNA sequence encoding the t-PA gene is depicted in FIG. 2 and described below.

Initially, a cDNA library was constructed mRNA isolated from to CHL-1 mRNA. The CHL-1 cDNA was digested with Bgl II and Xho II and inserted in Charon 4A, a lambda phage cloning vector (Maniatis, et al, Molecular Cloning, Cold Spring Harbor, 1982). A clone containing the Bgl II/Xho II fragment which extends from bp 187 to bp 2161 of the coding sequence in RNA t-PA was identified by hybridization to oligonucleotide probes.

The Bgl II/Xho II fragment corresponding to bp 187 to 2161 disclosed in the published t-PA cDNA sequence was removed from the Charon A4 clone and subcloned into pUC19 to yield pPA104.

The subcloned Bgl II/Xho II cDNA fragment from pPA104, contains sequences which code for the mature form of the t-PA protein but do not contain sequences for the pre- and pro-peptides of t-PA, that are required for secretion of the active protein. In order to express and secrete the mature and active form of t-PA in transfected cells, it was necessary to provide sequences coding for the secretory process.

The sequences that encode the pre- and pro-peptides were obtained by isolating a genomic fragment from a human genomic lambda library. This library was screened using the 414 bp Pst I fragment from the t-PA cDNA as the target sequence on VX (Maniatis et al). A 4kb Bgl II genomic fragment was identified that contained the 5' end of the t-PA structural gene including a portion of the 5' untranslated sequences, and 105 nucleotides encoding the pre- and pro- peptides, separated by a large intron (FIG. 2a).

This 4kb Bgl II genomic fragment was subcloned from the lambda phage identified into plasmid pPA104, which already contained the cDNA Bgl II/Xho II fragment. The new intermediate was called pPA103. Plasmid PA103 contains a genomic/cDNA junction which is redundant in that subclone. This junction was removed by digesting pPA103 with Nar I since both the cDNA and the genomic 5' region contain a Nar I site. This Nar I fragment was then moved into the cDNA subclone, pPA104, at its equivalent Nar I site (FIG. 2b). This new intermediate, pPA115, then contained genomic sequences fused to the cDNA coding region of t-PA.

The genomic/cDNA t-PA gene was removed by digesting pPA115 with Bcl I and partial digestion with Bgl II. The Bcl I-Bgl II cassette was then inserted into the unique Bgl II site of pneo5 thus generating pPA003. Because the t-PA coding region contains both genomic (including introns and exons) and cDNA sequences, this gene construct is referred to as a hybrid t-PA gene.

This hybrid t-PA gene in pPA003 contains the 5' end of the gene including the 5' untranslated sequences of t-PA, the pre- and pro-coding regions, the intron between these regions, and the coding region for mature t-PA.

ii. Intermediate Plasmid pPA502

Plasmid pPA502 (FIG. 1) contains a genomic-cDNA hybrid gene coding for t-PA under control of the triple LTR promoter and the gene for hygromycin B resistance under control of the TK promoter. Plasmid pPA102 was used as the source of the LTR-t-PA sequences and was constructed as follows: pPA102 was made by cutting pPA003 at the Bcl I and Xho I sites which flank the neomycin resistance gene. The ends of the resulting DNA fragment were treated with the Klenow fragment of DNA polymerase. The blunt ended DNA fragment was religated, thus deleting the neo gene.

The source of the TK-hygromycin sequences was pHMR272, which was obtained from Dr. Monica Lusky of the Europ. Mol. Biol. Organization [EMBO], Postfach 1022.40 6900 Heidelburg 1, FRG. The TK-hygromycin insert is available from a number of sources and is generally described in Biochlinger and Dingleman, Mol. Cell. Biol. 2929-2931, 1984, which contains; a bacterial PI promoter followed by the TK promoter, the gene for hygromycin resistance, and finally the polyadenylation region of the TK gene. HMR272 was digested at its unique Hind III site located at the 3' end of the TK terminator. The DNA was treated with Klenow fragment and Bam HI linkers were ligated to the linearized DNA. Upon digestion with Bam HI, a DNA fragment 2.7kb in length containing the promoter and hygromycin gene was generated. pPA102 was partially digested with Bam HI. The Bam HI fragment containing TK-hmb was then cloned into the Bam HI site of pPA102 that follows the t-PA gene and the SV40 polyadenylation region.

iii. Intermediate Plasmid pSC662

The cassette that contains the SV40 promoter and dhfr gene was prepared by removing the dhfr gene from PSV2-dhfr (Subramani, et al., Mol Cell Biol., 1:854-864, 1981) by digestion with Hind III and Bam HI. This dhfr gene was ligated into the Hind III and Bam HI sites of pBr328 (BRL, Bethesda, Md). SV40 DNA (BRL Bethesda, Md.) was cut at the Hpa II and Hind III sites flanking the SV40 early promoter. This fragment was ligated to the Klenow treated Cla I site and the Hind III site of pBr328.

Excision of the SV40 promoter and dhfr gene cassette was accomplished by digestion with Pvu II and Bam HI and subcloned into pBr327 which had been cut with EcoRv and BamHI. This intermediate, pSC661, was then cut with EcoRI and Bam HI in order to subclone the SV40-dhfr cassette into a pUC18 derivative, pSC652, which had also been digested with EcoRI and Bam HI. Plasmid pSC652 was made from pUC18 by converting the Bam HI site into a Cla I site using a Bam HI-Cla I linker. This final subclone was called pSC662 and has Cal I sites flanking the entire SV40 promoter and dhfr cassette.

iv. Plasmids pPA509 and pPA510

Plasmids pPA509 and 510 (FIG. 1) contain; the dhfr gene under the control of a truncated SV40 early promoter starting at the SV40 Pvu II site; the t-PA genomic-cDNA hybrid gene operably linked to the LTR promoter; and the gene for hygromycin selection operably linked to the TK promoter. In pPA509 the dhfr gene is transcribed in the divergent direction from the t-PA gene, while in pPA510 transcription is in the same direction. Using pSC662 digested with Cla I, the SV40-dhfr gene cassette was cloned into the Cla I site of pPA502 (as described above) directly 5' to the triple LTR promoter and t-PA gene. The plasmid pPA509 was deposited in the ATCC on June 18, 1987, to be maintained for a period of thirty years pursuant to the Budapest Treaty and is designated as ATCC 67443.

v. Plasmids pPA518 and pPA519

Plasmids pPA518 and pPA519 (FIG. 1) contain the LTR - t-PA hybrid gene cassette and the TK - hmb gene cassette. In plasmid pPA518 the gene for hygromycin resistance is transcribed in the same direction as the t-PA gene. In plasmid pPA519 hygromycin resistance is transcribed in the convergent direction with respect to the t-PA gene.

In constructing pPA518 and pPA519 the TK - hmb gene cassette was taken from the plasmid pPA502 (described above) by digestion with Bam HI. This Bam HI-ended fragment was inserted in both orientations into the Bcl I site of pPA122, a plasmid which contains the Harvey's triple LTR promoter and genomic-cDNA hybrid t-PA gene. Plasmid PA122 is a derivative of pPA003 (previously described) and was constructed as follows: pPA003 was cut at its two Nru I sites and Bcl I linkers were ligated to the remaining plasmid fragment. The plasmid was then ligated to recircularize the DNA, generating clone pPA118. The sequences that were deleted contained almost all of the tetracycline resistance gene and half of the neomycin resistance gene. pPA118 was cut at each of its two Bcl I sites and religated to delete the rest of the neomycin resistance sequence and to generate a single Bcl I site. This clone, pPA119, was digested at the Bcl I site and at one of the two Bgl II sites by partial digestion to allow ligation of a Bcl I fragment containing the SV40 polyadenylation sequence (V.B. Reddy, et al., Science, 200:494, 1978) directly after the t-PA stop codon. The Bcl I fragment was isolated from a pUC8 subclone, pSC672, containing SV40 sequences extending from the SV40 PstI to Bam HI site and which include the poly adenylation sequences pSC672 has the unique SV40 Bam HI site converted to a Bcl I site by adding Bam HI-Bcl I converting linkers.

Plasmid PA122, was cut at the Bcl I site 3' to the t-PA gene and the Bam HI-ended TK-hygromycin cassette was cloned in both orientations with respect to the t-PA gene and its promoter generating pPA518 and pPA519.

vi. Plasmids pPA524 and pPA525

Plasmid pPA524 and pPA525 contain the LTR - tPA gene cassette and the TK - hmb cassette (FIG. 1). In pPA524 transcription of the hmb gene occurs in the same orientation as t-PA. In pPA525 the hmb gene is transcribed in the divergent orientation with respect to t-PA. The TK - hmb cassette was obtained from a subclone of the plasmid pPA502 (described above) called pPA127. ppA127 was made by ligating Cla I-Bam HI converting linkers to pPA502 digested with Bam HI and allowing the plasmid to recircularize with Cla I sites now flanking the TK-Hmb sequences. The plasmid pPA127, therefore, when cut with Cla I allows removal of the whole TK-Hmb cassette. These TK-hmb sequences were cloned into the Cla I site 5' to the triple LTR promoter of pPA122 (described above) which contains the LTR - t-PA gene cassette. This plasmid has sequences deleted downstream from the t-PA gene which were not deleted in the similar plasmid pPA102, used in making pPA502. The TK-hmb cassette was cloned into the Cla I site in both orientations generating pPA524 and pPA525.

vii. Plasmids pPA208 and pPA209

Plasmids pPA208 and 209 contain the LTR - t-PA gene cassettte and the wild type dhfr gene as a selection marker under the control of a truncated SV40 promoter (FIG. 1). Plasmid pPA208, contains the dhfr gene so that it is transcribed in the same direction as the t-PA gene. In plasmid pPA 209 the dhfr gene is transcribed in the divergent orientation with respect to t-PA.

The cassette that contains the SV40 promoter and dhfr gene was excised from. pSC614. Plasmid pSC614 was produced by removing the dhfr gene from PSV2-dhfr (Subramani, et al., Mol Cell Biol, 1:854-864, 1981) by digestion with Hind III and Bam HI. This dhfr gene was ligated into the Hind III and Bam HI sites of pBR328 (BRL, Bethesda, Md). SV40 DNA (BRL Bethesda, Md.) was cut at the Hpa II site and Hind III sites flanking the SV40 early promoter. This fragment was ligated to the Klenow treated CIa I site and the Hind III site of pBR328.

Excision of the SV40 promoter - dhfr gene cassette was accomplished by cutting pSC614 with Pvu II and Bam HI, then filling in the Bam HI site using Klenow fragment of DNA polymerase and then adding Cla I linkers to each end.

The Cla I-ended DNA carrying the sequences for the SV40 promoter and the dhfr gene were cloned into the Cla I site 5' to the LTR - t-PA gene cassette of pPA102 (described above).

Plasmids containing the inserted fragment in either orientation were recovered as pPA208 and pPA209.

viii. plasmids pPA206 and pPA207

Plasmids pPA206 and pPA207 contain the LTR - t-PA gene cassette; the TK - neo gene cassette; and the SV40 - wild-type dhfr gene cassette (FIG. 1). In pPA206, the dhfr gene is transcribed in the same direction as the t-PA and neomycin resistance genes. In pPA207, the dhfr gene is transcribed in the divergent orientation with respect to t-PA.

To make these plasmids, a cassette for the SV40-dhfr sequences was cloned into the parent plasmid pPAO17 which contains the t-PA and neomycin resistance genes.

pPA017 was made by inserting the TK promoter into pPA003 at the unique Bcl I site which is located behind the polyA sequences which code for termination of t-PA and in front of the sequence coding for neomycin resistence. The Cla I site preceding the triple LTR promoter was cut and an SV40-dhfr cassette with Cla I linkers was cloned into the site in both orientations.

The previously described plasmid pSC614 was used for removal of the the cassette as follows: Digestion with Nru I at the two Nru I sites which flank the SV-dhfr sequences produces blunt ended fragments. One of the Nru I sites is in the pPR328 sequence that precedes the SV40 promoter and so additional chloramphenicol resistance sequence was carried along. The downstream Nru I site was located in the pBR322 tetracyline sequence and so additional sequence from that area was carried along as well. This fragment however contains the entire SV40 promoter starting at the SV40 Kpn site rather than the Pvu II site as described in pPA208, and pPA209. To these blunt ends we added Cla I linkers and cloned directly into the Cla I-digested pPA017 in both orientations.

ix. plasmid pPA202

Plasmid pPA202 contains the dhfr-IV gene under control of the SV40 promoter; a genomic-cDNA hybrid t-PA gene under control of the the triple LTR promoter, and a neomycin resistance gene under control of the TK promoter (FIG. 1). In pPA202 transcription for the mutant dhfr proceeds in the divergent direction from the t-PA and neo genes.

The dhfr-IV gene was derived from the wild type mouse dhfr gene. By in vitro mutagenesis of the gene sequence, an enzyme with altered characteristics was isolated. This mutant enzyme has a decreased affinity for MTX. To make plasmid pPA202, a casette containing the SV40 promoter and dhfr-IV sequence was cloned into the parent plasmid pPA017 which contains the t-PA and neomycin resistance genes.

Plasmid pSC637 was the source of the SV40 promoter and dhfr-IV gene cassette. To construct pSC637, we used a 300 bp fragment which contains an Xba I site followed by 10 basepairs of 5' untranslated sequence followed by the ATG and coding sequence for dhfr-IV. The 300 bp fragment ends at the equivalent to the wild-type dhfr Sac I site. The Xba I/Sac I fragment was first subcloned into pUC19 and was subsequently removed by digestion with Hind III and Sac I to accomodate cloning into the Hind III and Sac I sites of pSC614.

As in the retrieval of the SV40-wild-type-dhfr cassette described in construction of pPA206 and pPA207, the Nru I sites flanking the SV40 promoter and dhfr-IV sequences were digested and Cla I linkers were added for cloning into pPA017 at the Cla I site 5' to the triple LTR promoter. The resultant plasmid, pPA202, was deposited with the ATCC on June 16, 1987 and assigned deposit number ATCC 67446.

C. Host Cells

Two different cell lines are utilized. CHL-1 (A.T.C.C. Accession No. CRL 9446) is the cell line used for most of these experiments CHL-1 is a derivative of RPMI 7932 cells described in the detailed description. A second cell line, CHL-2 (A.T.C.C. Accession No. CRL 9451) is derived from CHL-1 by a previous transfection with pl'A003. This stably transfected cell line produces t-PA at a rate of 0.20-0.35 mU/cell/day; about 2-3 times more than the parent CHL-1.

D. Transfection & Selection of Clones

For each transfection described, 5 µg of plasmid DNA, was precipitated with CaCl2, by the method of Wigler et al., (Cell 16:777-785, 1979) and added to a monolayer of $5 \times 10^5$ CHL-1 host cells in 6 well plates. Forty-eight hours after transfection, a known number of cells are plated onto selective media. In one embodiment, comprising the neo gene, the selection marker confers resistance to G418 at a concentration of 1.0 mg/ml. Clones which demonstrated a resistance to 1.0 mg/ml G418 were identified and isolated 3 to 4 weeks following transfection In a second embodiment, resistance to hygromycin B is used as the selection marker. CHL-1 cells transfected with the bacterial hmb gene can survive growth in 0.3 mg/ml hygromycin B.

In another embodiment, the selectable phenotype is the expression of dhfr which confers upon the transfected cell the ability to grow in the presence of 100 nM MTX in the absence of nucleotides. The action of MTX is to inhibit dhfr thus blocking the synthesis of nucleosides triphosphate precursors of DNA biosynthesis.

The transfection or selection frequency is determined as the number of colonies arising after selection, divided by the total number of cells plated.

E. Amplification

A population of cells resistant to the first selection conditions (G418 or hygromycin B) were subjected to a second round of selective pressure. Either 100nM or 500nM MTX was added to the growth medium to select for transfectants that expressed the dhfr gene. Only clones which had amplified the dhfr gene would be able to grow in this high level of MTX. In the process of gene amplification, other plasmid sequences will be co-amplified with the dhfr gene and thus lead to increased gene expression of the non-selectable gene as well. Resistant clones were apparent after 4 to 6 weeks. Individual clones resistant to these levels of MTX were isolated and assayed, and a pooled population was plated into a ten-fold greater concentration of MTX (1µM or 5µM). Clones were again recovered from this selection step and assayed.

F. t-PA Assay

Cells that had taken up plasmid DNA during transfection and were able to grow in the appropriate selection medium formed clones on 100 mm petri dishes. These clones were either individually isolated or pooled together as a population in order to assay for t-PA expression.

The assay for t-PA production was carried out in medium containing 0.1% fetal bovine serum and 10 KIU/ml aprotinin. T-PA produotion in 24 hours was determined for a known number of cells. Aliquots of cell culture supernatant after a 24 hour production period were saved and the number of cells in the culture was counted. For the t-PA analysis, 5 µl samples of culture supernatant were placed in a circular well excised from an agarose matrix containing sheep fibrinogen, human thrombin and human plasminogen. A clearing around the circle of culture supernatant was interpreted as conversion of plasminogen to plasmin which had digested the fibrin, all initiated by the presence of t-PA. (Suck, D., et al., PNAS USA, 78:4319-4323, 1981.) The size of the clearing, thus, correlates with the amount of t-PA in the sample. The values given in the tables are obtained by dividing the t-PA units in the supernatant by the number of cells in the culture.

i. Enhanced Expression Levels Where the Selectable Marker is Placed Either 5' or 3' to the t-PA Gene.

To determine the effect of the position and orientation of the selectable marker on expression of the t-PA gene, the series of plasmids pPA518, pPA519, ppA524, and pPA525 were used to transfect CHL-1 cells. Table I shows the level of t-PA production of cell population following transfection and selection with hygromycin. The level of t-PA expression in the populations was initially more than twice as high for pPA525 than for any of the other plasmids Plasmids pPA518, pPA519 and pPA524 had similar levels of t-PA in several different assays and experiments These results indicate that both the orientation and position of the gene cassettes effect expression levels. In pPA518 and pPA519 the selection marker was inserted 3' to the t-PA gene in both orientations with respect to the t-PA gene. At this position the orientation does not effect expression of the t-PA gene. However, with pPA524 to pPA525, the selection marker was inserted 5' to the t-PA gene, and the effect of gene orientation on t-PA expression is marked and reproducible.

ii. Enhanced t-PA Expression is Due to Gene Orientation and is Unaffected By the Choic of Host Cells.

In order to assess the transcription frequency of the series of t-PA expression plasmids described in F.i., a fibrin-agarose overlay assay was used to quantitate t-PA expression in a population of transfected cells. To eliminate background t-PA expression from host cells, the mouse cell line C127 (ATCC CRL1616) was used for this assay, because C127 cells do not produce any endogenous t-PA. Ten μg of each plasmid was used to transfect $10^6$ C127 cells in a 100 mm plate following the standard transfection protocol outlined above. Twenty-four hours following transfection of these cells, the cells were divided among a series of duplicate 100 mm dishes at densities of $10^4$, $3\times10^4$, $10^5$, $3\times10^5$, and $10^6$ cells per plate. No selective agent was added to the cells. Hygromycin (0.2 mg/ml) was added to a second plate containing $10^6$ cells to determine the transfection frequency for this series of plasmids in C127 cells. The next day, the cell monolayers were over laid with a fibrin-agarose solution. One week later the number of clearings on each plate was determined.

The fibrin-agarose overlay was prepared as follows (10 ml total).

1. 5 ml 2.4% loW melt agarose (Bio-Rad) dissolved in $H_2O$, sterilized and kept at 42°;
2. 3 ml 10 mg/ml sheep fibrinogen (Sigma) dissolved in warm $H_2O$ and filter sterilized
3. 2 ml 5×MEM containing 50% FBS and 5×antibiotics plus 1 unit of bovine thrombin (Sigma)

The clearings in the fibrin overlay are due to the production of t-PA by the transfected cells. The t-PA secreted by the cell activates the plasminogen present in the serum and the active plasmin cleaves the clotted fibrin to produce a clearing. Thus, the number of clearings is proportional to number of transfected cells that are producing t-PA. Since the transfection frequency of all plasmids was similar (about $10^{-4}$ clones/cell), the number of clearings is proportional to the number of cells that are producing detectable amounts of t-PA and not to the number of transfected cells in the population.

A comparison of the levels of t-PA expressed by each plasmid was obtained by plotting the number of clearings per plate vs. the number of cells per plate. The results of this analysis is shown in FIG. 4. It can be seen that there are significantly more clearings detected with pPA525 than the other plasmids. The two plasmids pPA518 and pPA519 have similar numbers of clearings at each cell density while pPA524 has slightly more than pPA518 and pPA519 but half that of pPA525.

In this example, both pPA524 and pPA525 were more efficient in generating colonies that produced detectable levels of t-PA than either pPA518 or ppA519. This result suggests that position of the selection marker does influence t-PA expression. Moreover, the number of clearings seen with pPA525 was greater than with pPA524 indicating that gene orientation in the divergent form has a positive effect on expression of t-PA. This example demonstrates that the enhanced differential t-PA expression due to gene orientation described in example F.i. is not restricted to the CHL-1 cell line.

iii Enhanced t-PA Expression is Not Affected By the Choice of Selectable Marker.

Plasmids pPA208 and pPA209 were constructed so that the dhfr gene can be used as the selection marker in place of hygromycin. Plasmid pPA208 contains the dhfr gene and the t-PA genes in the same orientation; in ppA209 the genes are in the divergent orientation. These t-PA expression plasmids were analyzed to determine if the effect of gene orientation was specific for the hygromycin resistance gene or if other selection markers can be substituted.

This pair of plasmids was used to transfect CHL-1 cells and clones were selected in 100 nM MTX in medium lacking nucleosides. pSC614, a dhfr plasmid without t-PA sequences, and salmon sperm DNA were used as transfection controls The transfection frequency and the t-PA production level of the mass cultures were determined. Plasmid pPA209 yielded a transfection frequency ten-fold higher than did plasmid pPA208. Further, t-PA production in the mass culture was determined to be twice as high for the pPA209 transfectants than for the pPA208 transfectants (Table IIA).

Individual clones from the cultures described in Table IIA were isolated and assayed for t-PA production. Table IIB shows these results. The clones with the highest expression of the t-PA gene are derived from transfections with pPA209. The level of t-PA expression for pPA208 transfectants ranges from 0.0–1.0 mU/cell/day, while the level of t-PA expression for pPA209 transfectants in CHL-1 cells was found to be as high as 2.0–2.5 mU/cell/day. The results described in this example agree with the previous examples. In this example, when the selective marker is in the 5' position with respect to the t-PA gene, the plasmid with the divergent transcription orientation resulted a in higher transfection frequency as well as clones with higher t-PA expression levels.

iv. Enhanced Expression of t-PA Due to Plasmids Containing More Than One Selection Marker; Wherein A First Selection Marker is in the Convergent Orientation to the t-PA Gene and the Orientation of A Second Selection Marker is Varied.

Plasmids pPA509, and pPA510 each contain two selection markers, hygromycin and dhfr, along with the t-PA gene. In both plasmids, the hygromycin gene and its promoter is inserted 3' to the t-PA gene, in the convergent transcription orientation. The transcription of the dhfr gene is in the same orientation as the t-PA gene in pPA510, while dhfr and t-PA are in divergent transcription orientations in pPA509. In the following examples, the hygromycin gene was used first to select clones. Following the initial selection, clones were then selected with MTX.

These plasmids, pPA509 and pPA510, were transfected into CHL-1 and CHL-2 cells as described above. CHL-2 is a derivative of CHL-1 which contains ppA003. The t-PA production is increased over CHL-1 from 0.1 mu/cell/day to 0.25–0.3 mu/cell/day. For each transfection the level of t-PA production in the mass culture was determined. These values (Table IIIA) show that when hygromycin is used as the selective agent transfectants derived from both plasmids display virtually identical levels of t-PA expression. However, when the selective agent was changed to 500 nM MTX, the effect of gene orientation on t-PA expression becomes obvious. In the CHL-1 transfected cells, pPA509 induces t-PA expression at a level almost twice as high (2.1 mu/cell/day) as pPA510 (1.2 mu/cell/day). A similar difference in t-PA expression levels is seen in CHL-2 transfected cells. These results indicate that when selective pressure is placed on the marker gene in the divergent orientation with respect to the t-PA, the mass population of clones produce higher levels of t-PA as seen in F.i. and F.iii.

This observation from mass culture data is substantiated by an analysis of individual clones. Table IIIB shows the transfection frequencies and levels of t-PA expression for individual clones selected from the transfection in CHL-1 cells. When hygromycin is used as the selective agent, pPA509 and pPA510 each gave approximately the same number of clones. Of the 24 clones that were assayed, all expressed t-PA at levels within the same range for each plasmid used. Again, this result is expected since the t-PA and hygromycin genes are oriented identically in both plasmids. However, when the selective agent was changed to 500nM MTX, the number of clones observed differed by a factor of ten. Individual clones were isolated and assayed for t-PA production. In this analysis, clones that produce higher levels of t-PA were isolated only with pPA509.

T-PA levels for individual clones resulting from transfections into CHL-2 with pPA509 and pPA510 follow the same pattern (Table III C). When hygromycin was the selective agent, t-PA levels in clones from pPA509 and pPA510 were identical. However, when the dhfr gene was used as the selective marker, clones from the pPA509 transfection gave more clones and they had higher levels of t-PA (over 15 mu/c/d). Moreover, the increase in t-PA expression by the highest clones derived from CHL-2 is almost 5 times greater than the highest clone from CHL-1 (compare Table IIIC with IIIB). This larger increase is not expected from the production levels of the two host cell lines. These t-PA expressing clones are further discussed in Example VII.

The data shows clearly that when gene orientation is not an issue, as in the case of hygromycin selection, both plasmids (pPA509 and pPA510) yielded the same number of clones with the similar t-PA expression levels. This observation is valid when either mass cultures or individual clones are analyzed. It is also true with CHL-1 or CHL-2 as the host cells. selectable gene (t-PA) becomes apparent when the selection marker is present at the 5' position and in two different orientations. Thus, when selective pressure is placed on the dhfr gene by growth in MTX, differences are seen in transfection frequencies which is a measure of dhfr gene function and also in t-PA expression efficiency. This result indicates that when both the dhfr and t-PA genes are in the same orientation, the expression of both genes is depressed.

v. Enhanced Exoression of t-PA Due to Plasmids Containing More Than One Selection Marker; Wherein A First Selection Marker is in the Same Orientation as the t-PA Gene and the Orientation of A Second Selection Marker is Varied.

Plasmids pPA206 and pPA207 are t-PA expression plasmids that also have two selection markers: neo and dhfr. Using these two plasmids, we were able to compare the results in t-PA expression of selection using genes having a fixed arrangement (neo) to selection using genes having either the same or the opposite arrangement (dhfr). This experiment was carried out in CHL-1 cells (Table V). The neo gene in both pPA206 and pPA207 is oriented in the same direction of transcription as the t-PA gene. When selected in G418 alone, the t-PA expression in the mass culture showed little difference between the two plasmids.

The transcription orientation of the dhfr gene relative to the t-PA gene is in the same direction in pPA206 and in the divergent orientation in pPA207. When the selective agent was switched to 100nM MTX, the effect of the gene orientation is seen. The determinations of t-PA production in the mass cultures show that for pPA207 transfectants, this level is four times greater (1.322 mU/cell/day) than that of pPA206 transfectants (0.322 mU/cell/day). When individual transfectants are analyzed, the range of clones expressing t-PA is shifted to higher levels for pPA207 transfectants. The highest clone was producing 6.7 mU/cell/day of t-PA.

vi. Enhanced Exoression of t-PA Due to Gene Orientation in an Alternative Eukarvotic Cell Line.

CHO dhfr-cells were transfected with pPA206 and pPA207 plasmids and selected for growth in media lacking nucleosides (Kaufman, R., and Sharp, P., J. Mol. Biol., 159:601-621, 1982). Individual clones were then assayed for productivity (FIG. 5). The transfectants from pPA207 had more clones producing higher levels of t-PA in the initial screen and had a range of clones with greater levels of t-PA synthesis than pPA206 transfectants. The finding from this experiment is consistent with Examples F.iii. and v. in that the different orientation of the dhfr gene in pPA207 and pPA206 has an marked effect on t-PA production.

This example also demonstrates that the increased t-PA expression observed with plasmids having the selection marker in a divergent transcription orientation is not restricted to host cell or selection marker. Examples F.i., ii., and vi. together show that the effect of gene orientation can be demonstrated in three different cell lines from human, mouse, and hamster. Moreover, this effect is seen when either hygromycin or dhfr is used as the selection marker. cl vii. Use of Gene Orientation Methods and Amplification to Increase Levels of t-PA Expression.

The t-PA expression levels of the clones described in Example F.iv. were increased by stepwise selection in MTX. Initially, a mass population was generated by transfection of CHL-1 cells with pPA509. This population of hygromycin resistant clones was then selected in 100 nM MTX. The mass culture of 100 nM MTX resistant clones was then subjected to a second round of amplification in 1 µM MTX. From this selection procedure two new clones were isolated W8A5 and W8A6. They were propagated in the absence and presence of 1 µM MTX. W8A5 without MTX grew very well and initially produced very high levels of t-PA (5 mU/c/d) (Table V). However, the expression level decreased with growth in the absence of selective pressure (down to 1.8 mU/c/d). This culture was then reselected in 1 µM MTX and yielded clones W8A5-1, and W8A5-3.

Clones W10A5, 11, 12, 17, 21 and 24 were derived by transfecting plasmid pPA509 into CHL-2 cells and selecting for hmb resistance (Example F.iv.). A mass population of hygromycin resistant clones were selected in 500 nM MTX and expressed very high levels of t-PA. Individual clones were isolated from this population in 500 nM MTX and the clones W10A5, W10AII, W10A12, W10A17, W10A21 and W10A24 were analyzed for t-PA expression.

Additionally, plasmid pPA202 was used for a similar experiment. This plasmid carries two selection markers, dhfr-IV and neo. The dhfr-IV gene under the control of the SVe promoter was inserted 5' to the t-PA gene and is transcribed in a divergent direction with respect to t-PA. The neo gene, under control of the TK promoter, was inserted 3' to the t-PA gene and is transcribed convergent to t-PA. No paired plasmid with reverse orientation was constructed. CHL-1 cells were transfected with pPA202 and transfectants were selected with neomycin. One clone was isolated which produced tPA at a level of 0.3 mU/c/d, K25-5' (Table V). This clone was then reselected in 1 µM MTX in medium without nucleosides. One clone was isolated that produced t-PA at 4.0 mu/c/d. This clone was subcloned again in 1 μM MTX without nucleosides and a third isolate was obtained (K25-5-1-15) which produced t-PA at 7 mu/c/d. Selection using the marker transcribed in a divergent orientataion (DHFR -IV) yielded transfectants having a higher level of t-PA expression than transfectants selected on the basis of the convergent gene (neo).

TABLE I

T-PA Expression Levels in mu/cell/day of mass populations of CHL-1 cells transfected as follows:

| Plasmid | t-PA |
|---|---|
| pPA 518 | .237 |
| pPA 519 | .415 |
| pPA 524 | .394 |
| pPA 525 | .870 |
| CHL-1 | .098 |

TABLE IIA

| Selection | Plasmid | Transfection Frequency | t-PA Production of Mass Cultures mU/cell/day |
|---|---|---|---|
| 100 nM Mtx | pPA 208 | $2 \times 10^{-5}$ | 0.76 |
| | pPA 209 | $2 \times 10^{-4}$ | 1.44 |
| | pSC 614 | $<2 \times 10^{-5}$ | N.D. |
| | s. sperm | $<2 \times 10^{-5}$ | N.D. |

Plasmids were transfected into CHL-1 Cells.
The t-PA production level in CHL-1 cells was 0.11 mU/cell/day.

TABLE IIB

| CHL-1 Transfectants | | # of clones assayed | t-PA Production in mU/cell/day # of clones in each range | | | | | |
|---|---|---|---|---|---|---|---|---|
| Selection | plasmid | | 0-0.2 | 0.3-0.5 | 0.6-1.0 | 1.1-1.5 | 1.6-2.0 | 2.1-2.5 |
| 100 nM Mtx | pPA208 | 6 | 3 | 1 | 2 | | | |
| | pPA209 | 25 | 6 | 7 | 9 | 1 | 1 | 1 |
| | pSC614 | 7 | 7 | | | | | |
| | s. sperm | 8 | 8 | | | | | |

TABLE IIIA

| | | t-PA Production of Mass Cultures in mU/cell/day | |
|---|---|---|---|
| selection | plasmid | CHL-1 | CHL-2 |
| hygromycin | pPA509 | 0.3 | 1.4 |
| | pPA510 | 0.2 | 1.4 |
| 500 nM Mtx | pPA509 | 2.1 | 15.7 |
| | pPA510 | 1.2 | 10.8 |

TABLE IIIB

| Experiment W8: CHL-1 Cells | | | t-PA Production in mU/cell/day # of clones in each range | | | | | | | |
|---|---|---|---|---|---|---|---|---|---|---|
| Selection/ plasmid | selection frequency | # of clones assayed | 0-1.9 | 2.0-3.9 | 4.0-5.9 | 6.0-7.9 | 8.0-9.9 | 10.0-11.9 | 12.0-13.9 | 14.0-15.9 |
| hygromycin | | | | | | | | | | |
| pPA509 | $6 \times 10^{-4}$ | 24 | 24 | | | | | | | |
| pPA510 | $7 \times 10^{-4}$ | 24 | 24 | | | | | | | |
| 500 nM Mtx | | | | | | | | | | |
| pPA509 | $1 \times 10^{-3}$ | 11 | 7 | 4 | | | | | | |
| pPA510 | $1.2 \times 10^{-4}$ | 4 | 4 | | | | | | | |

TABLE IIIC

| Experiment W10: CHL-2 Cells | | | t-PA Production in mU/cell/day # of clones in each range | | | | | | | |
|---|---|---|---|---|---|---|---|---|---|---|
| Selection/ plasmid | selection frequency | # of clones assayed | 0-1.9 | 2.0-3.9 | 4.0-5.9 | 6.0-7.9 | 8.0-9.9 | 10.0-11.9 | 12.0-13.9 | 14.0-15.9 |
| hygromycin | | | | | | | | | | |
| pPA509 | $2 \times 10^{-3}$ | 12 | 11 | 1 | | | | | | |
| pPA510 | $3.6 \times 10^{-3}$ | 12 | 11 | 1 | | | | | | |
| 500 nM Mtx | | | | | | | | | | |
| pPA509 | $1.2 \times 10^{-4}$ | 22 | | | 3 | 6 | 8 | 2 | 1 | 2 |
| pPA510 | $5 \times 10^{-5}$ | 29 | 1 | 8 | 15 | 3 | | | 2 | |

TABLE IV

| | | | t-PA Production of Transfected Cultures of CHL-1 Cells | | | | | | | | |
|---|---|---|---|---|---|---|---|---|---|---|---|
| Transfected Plasmid | Primary Selection | Secondary Selection | t-PA Production of Mass Cultures (mU/cell/day) | # of Clones Assayed | t-PA Production of Clones # of Clones in each range (mU/cell/day) | | | | | | |
| | | | | | 0-1.0 | 1.1-2.0 | 2.1-3.0 | 3.1-4.0 | 4.1-5.0 | 5.1-6.0 | 6.1-7.0 |
| pPA206 | G418 | N.D. | 0.19 | 0 | | | | | | | |
| pPA207 | G418 | N.D. | 0.30 | 0 | | | | | | | |
| pPA206 | G418 | 100 nM Mtx | 0.33 | 15 | 13 | 2 | | | | | |
| pPA207 | G418 | 100 nM Mtx | 1.32 | 21 | 13 | 5 | | 1 | | | 1 |

TABLE V

| Clone | Plasmid | Host Cell | Selection Steps | t-PA Producti (mU/cell/day) |
|---|---|---|---|---|
| W8A5 | pPA509 | CHL-1 | hmb, 100 nM Mtx, 1 μM Mtx | 1.8-11.0 |

TABLE V-continued

| Clone | Plasmid | Host Cell | Selection Steps | t-PA Producti (mU/cell/day) |
| --- | --- | --- | --- | --- |
| W8A5-1 | pPA509 | CHL-1 | hmb, 100 nM Mtx, 1 µM Mtx, 1 µM Mtx | 9.3–15.2 |
| W8A5-3 | pPA509 | CHL-1 | hmb, 100 nM Mtx, 1 µM Mtx, 1 µM Mtx | 7.1–14.6 |
| W8A6 | pPA509 | CHL-1 | hmb, 100 nM Mtx, 1 µM Mtx | 2.7–12.4 |
| W10A5 | pPA509 | CHL-2 | hmb, 500 nM Mtx | 10.3–16.5 |
| W10A11 | pPA509 | CHL-2 | hmb, 500 nM Mtx | 7.6–10.3 |
| W10A12 | pPA509 | CHL-2 | hmb, 500 nM Mtx | 9.0–9.7 |
| W10A17 | pPA509 | CHL-2 | hmb, 500 nM Mtx | 8.3–16.0 |
| W10A21 | pPA509 | CHL-2 | hmb, 500 nM Mtx | 11.2–20.5 |
| W10A24 | pPA509 | CHL-2 | hmb, 500 nM Mtx | 9.4–18.4 |
| K25-5 | pPA202 | CHL-1 | G418 | 0.3 |
| K25-5-1 | pPA202 | CHL-1 | G418, 1 µM Mtx | 4 |
| K25-5-15 | pPA202 | CHL-1 | G418, 1 µM Mtx, 1 µM Mtx | 7 |

What is claimed is:

1. A eukaryote cell transfected with a genetically engineered plasmid, said plasmid comprising:
   a selectable gene cassette and
   a second gene cassette comprising an LTR promotor controlling the expression of a nucleic acid sequence encoding a desired gene product qwherein the selectable gene cassette and the second gene cassette are adjacent to each other in opposite and divergent transcriptional orientation such that higher levels of protein expression for said second gene are produced when selective pressue is applied to the cell said pressure being specific for the selectable gene cassette and wherein the higher levels of expression are relative to identically situated plasmids having the selectable gene cassette and the second gene cassette oriented in the same transcriptional direction.

2. The dukaryotic cell line of claim 1 wherein said second gene encodes a pharmaceutically active protein for human use.

3. The eukaryotic cell line of claim 1 wherein said second gene encodes a protein selected from the group consisting of hormones, immunogens, anti-cancer agents, antibiotics, immunoglobulins, and anti-allergy agents.

4. The eukaryotic cell line of claim 3 wehrein said second gene encodes a thrombolytic protein.

5. The eukaryotic cell line of claim 4 wherein said second gene encodes t-PA.

6. The eukaryotic cell line of claim 1 wherein said second gene encodes an immunogen.

7. The eukaryotic cell line of claim 5 wherein said cell line is selected from the group consisting of K25-5-1-15, W8A5-1, and W10A21.

8. The eukaryotic cell line of claim 1 wherein said cell line is selected from the group consisting of mammalian cells, insect cells, and yeast cells.

9. A recombinant plasmid capable of being transfected into eukaryotic cells said plasmid comprising:
   a selectable gene cassette and
   a second gene cassette comprising an LTR promoter controlling the transcription of a nucleic acid sequence encoding a desired gene product whereint he selectable gene cassette and the second gene cassette are adjacent to each other in opposite and divergent transcriptional orientation such that higher levels of protein expression for the second gene are produced when selective pressure is applied to the cell said pressure being specific for the selectable gene cassette and wherein the higher levels of expression are relative to identically situated plasmids having the selectable gene cassette and said second gene cassette oriented in the same transcriptional direction.

10. The recombinant plasmid of claim 9 wherein said second gene encodes a pharmaceutically active protein for human use selected from the group consisting of hormones, immunogens, anti-cancer agents, antibiotics, immunoglobulines, and anti-allergy agents.

11. The recombinant plasmid of claim 9 wherein said second gene encodes a thrombolytic protein.

12. The recombinant plasmid of claim 11 wherein said second gene encodes t-PA.

13. The recombinant plasmid of claim 9 wherein said second gene encodes an immunogen.

14. The recombinant plasmid of claim 12 wherein said plasmid is selected from the group consisting of pPA509 (ATCC 67554), or pPA202 (ATCC 67446).

15. A method for producing a desired protein comprising transfecting a eukaryotic host cell with a recombinasnt plasmid comprising:
   (a) a selectable gene cassette; and
   (b) a second gene cassette comprising an LTR promotor controlling the transcription of a nucleic acid sequence encoding a desired protein;
   wherein the selectable gene cassette and the second gene cassettes are adjacent to each other in oppoiste and divergent transcriptional orientation; applying selective pressure specific for the selectable gene cassette; and culturing the cells under conditions which permit expression of the protein.

16. The method according to claim 15 wherein said selectable gene is selected from the group consisting of genes encoding dihydrofolate reductase, neomycin phosphotransferase, and hygromycin phosphotransferase.

17. The method of claim 15, wherein the host cells are selected from the group consisting of mammalian cells, insect cells, or yeast cells.

18. The method of claim 15 wherein the desired protein is a human pharmaceutical.

19. The method of claim 17 wherein the eukaryotic host cell contains an endogenous gene encoding said desired protein.

20. A human cell line derived from RPMI 7932 wherein said cell line is characterised as
   (a) substantially free of mycoplasma contamination;
   (b) capable of growth to a density of $5 \times 10^7$ cells/ml in a suspension culture; and
   (c) capable of bead to bead transfer.

21. The cell line of claim 20 designated as CHL-1ATCC (CRL 9446).

* * * * *

UNITED STATES PATENT AND TRADEMARK OFFICE
CERTIFICATE OF CORRECTION

PATENT NO. : 5,017,478
DATED : May 21, 1991
INVENTOR(S) : Cashion et al.

Page 1 of 5

It is certified that error appears in the above-identified patent and that said Letters Patent is hereby corrected as shown below:

In column 1, line 9, delete "074/083" and substitute therefor, --074,083--;

In column 1, lines 25-26, "2. Background and Prior Art" should be shown as a subheading;

In column 1, line 28, delete "eukaxyotic" and substitute therefor, --eukaryotic--;

In column 2, line 12, delete "tWo" and substitute therefor, --two--;

In column 3, line 17, delete "diagramat" and substitute therefor, --diagramatic--;

In column 3, line 19, delete "pPa209" and substitute therefor, --pPA209--;

In column 3, line 19, delete "pPa202" and substitute therefor, --pPA202--;

In column 3, line 46, delete "perti" and substitute therefor, --petri--;

In column 4, line 33, delete "ppA003" and substitute therefor, --pPA003--;

In column 5, line 41, delete "aminal" and substitute therefor, --animal--;

In column 6, line 42, delete "dihyrofolate" and substitute therefor, --dihydrofolate--;

In column 6, line 51, delete "Was" and substitute therefor, --was--;

In column 8, line 3, delete "; cells/ml" and substitute therefor, --cells/ml--;

In column 8, line 32, delete "such as Ti." and substitute therefor, --such as--;

In column 8, line 8, delete "pietin," and substitute therefor, --poietin--;

UNITED STATES PATENT AND TRADEMARK OFFICE
CERTIFICATE OF CORRECTION

PATENT NO. : 5,017,478

DATED : May 21, 1991

INVENTOR(S) : Cashion et al.

It is certified that error appears in the above-identified patent and that said Letters Patent is hereby corrected as shown below:

In column 8, line 59, delete "include by are" and substitute therefor, --include but are--;
In column 8, line 61, delete "erythropoetin" and substitute therefor, --erythropoietin--;
In column 9, line 12, delete "GALI,10" and substitute therefor, --GAL1,10--;
In column 9, line 26, delete "Pubklishers" and substitute therefor, --Publishers--;
In column 9, line 27, delete "wherein" and substitute therefor, --herein--;
In column 11, line 18, delete "to to a" and substitute therefor, --to a--;
In column 11, line 48, delete "known in the are" and substitute therefor, --known in the art--;
In column 11, line 60, delete "selection" and substitute therefor, --section--;
In column 12, line 18, delete "A. Desiqn" and substitute therefor, --A. Design--;
In column 12, line 40, delete "positons" and substitute therefor, --positions--;
In column 12, line 53, delete "discistronic" and substitute therefor, --dicistronic--;
In column 14, line 9, delete "Mol. Cell. Biol. 2929-2931" and substitute therefor, --Mol. Cell. Biol., 4:2929-2931--;
In column 14, line 45, delete "Cal I" and substitute therefor, --Cla I--;
In column 15, line 46, delete "ppA127 was" and substitute therefor, --pPA127 was--;

UNITED STATES PATENT AND TRADEMARK OFFICE
CERTIFICATE OF CORRECTION

PATENT NO. : 5,017,478

DATED : May 21, 1991

INVENTOR(S) : Cashion et al.

Page 3 of 5

It is certified that error appears in the above-identified patent and that said Letters Patent is hereby corrected as shown below:

In column 15, lines 49 and 51, delete "TK-Hmb" and substitute therefor, --TK-hmb--;

In column 16, line 33, delete "pPAO17" and substitute therefor, --pPA017--;

In column 16, line 46, delete "pPR328" and substitute therefor, --pBR328--;

In column 16, line 61, delete "the the triple" and substitute therefor, --the triple--;

In column 17, line 28, delete "experiments CHL-1" and substitute therefor, --experiments. CHL-1--;

In column 17, line 38, delete "CaCl2" and substitute therefor, --$CaCl_2$--;

In column 17, line 47, delete "transfection In" and substitute therefor, --transfection. In--;

In column 18, line 20, delete "produotion" and substitute therefor, --production--;

In column 18, line 47, delete "plasmids Plasmids" and substitute therefor, --plasmids. Plasmids--;

In column 18, line 49, delete "experiments These" and substitute therefor, --experiments. These--;

In column 18, line 61, delete "Choic of Host" and substitute therefor, --Choice of Host--;

In column 19, line 17, delete "loW" and substitute therefor, --low--;

In column 19, line 18, delete "$H^2O$" and substitute therefor, --$H_2O$--;

In column 19, line 46, delete "ppA519" and substitute therefor, --pPA519--;

In column 19, line 62, delete "ppA209" and substitute therefor, --pPA209--;

UNITED STATES PATENT AND TRADEMARK OFFICE
CERTIFICATE OF CORRECTION

PATENT NO. : 5,017,478  
DATED : May 21, 1991  
INVENTOR(S) : Cashion et al.

Page 4 of 5

It is certified that error appears in the above-identified patent and that said Letters Patent is hereby corrected as shown below:

In column 20, line 3, delete "controls The" and substitute therefor, --controls.  The--;
In column 20, line 22, delete "resulted a in" and substitute therefor, --resulted in a--;
In column 20, line 45, delete "ppA003" and substitute therefor --pPA003--;
In column 21, line 32, delete "host cells. selectable gene" and substitute therefor, --host cells.  The effect of gene orientation on expression of the non-selectable gene--;
In column 21, line 42, delete "Exoression" and substitute therefor, --Expression--;
In column 22, line 5, delete "Exoression" and substitute therefor, --Expression--;
In column 22, line 27, delete "cl" and move "vii. Use of Gene..." as a subparagraph heading.
In column 22, line 52, delete "W10AII" and substitute therefor, --W10A11--;
In column 23, line 5, delete "yieIded" and substitute therefor, --yielded--;
In claim 1, line 6, delete "qwherein" and substitute therefor, --wherein--;
In claim 2, line 1, delete "dukaryotic" and substitute therefor, --eukaryotic--;
In claim 4, line 1, delete "wehrein" and substitute therefor, --wherein--;
In claim 9, bridging lines 6 and 7, delete "whereint he" and substitute therefor, --wherein the--;
In claim 14, line 3, delete "(ATCC 67554)" and substitute therefor, --(ATCC 67443);

UNITED STATES PATENT AND TRADEMARK OFFICE
CERTIFICATE OF CORRECTION

PATENT NO. : 5,017,478

DATED : May 21, 1991

INVENTOR(S) : Cashion et al.

It is certified that error appears in the above-identified patent and that said Letters Patent is hereby corrected as shown below:

In claim 15, bridging lines 2 and 3, delete "recombinasnt" and substitute therefor, --recombinant--; and In claim 15, bridging lines 9 and 10, delete "oppoiste" and substitute therefor, --opposite--.

Signed and Sealed this

Fourteenth Day of June, 1994

*Attest:*

BRUCE LEHMAN

*Attesting Officer*     *Commissioner of Patents and Trademarks*